US008114606B2

(12) United States Patent
Cao

(10) Patent No.: US 8,114,606 B2
(45) Date of Patent: Feb. 14, 2012

(54) ARL-1 SPECIFIC ANTIBODIES

(75) Inventor: Deliang Cao, Chatham, IL (US)

(73) Assignee: The Board of Trustees of Southern Illinois University, Springfield, IL (US)

( * ) Notice: Subject to any disclaimer, the term of this patent is extended or adjusted under 35 U.S.C. 154(b) by 683 days.

(21) Appl. No.: 12/032,327

(22) Filed: Feb. 15, 2008

(65) Prior Publication Data

US 2008/0261223 A1 Oct. 23, 2008

Related U.S. Application Data

(60) Provisional application No. 60/890,414, filed on Feb. 16, 2007.

(51) Int. Cl.
*G01N 33/53* (2006.01)
*G01N 33/573* (2006.01)
*G01N 1/30* (2006.01)
*G01N 33/48* (2006.01)
*C12Q 1/26* (2006.01)
*C12N 9/04* (2006.01)
*C07K 7/08* (2006.01)
*C07K 16/40* (2006.01)

(52) U.S. Cl. ......... 435/7.1; 435/7.4; 435/25; 435/40.5; 435/40.51; 435/190; 435/960; 435/967; 435/975; 530/300; 530/326; 530/387.1; 530/388.1; 530/388.26; 530/403; 530/806; 530/828; 530/846; 530/866; 530/867

(58) Field of Classification Search ............... 435/7.1, 435/7.4, 25, 40.5, 40.51, 40.52, 190, 960, 435/967, 975; 530/300, 326, 387.1, 387.3, 530/388.1, 388.26, 403, 806, 828, 846, 866, 530/867
See application file for complete search history.

(56) References Cited

U.S. PATENT DOCUMENTS

| | | | |
|---|---|---|---|
| 4,196,265 A | 4/1980 | Koprowski et al. |
| 4,444,887 A | 4/1984 | Hoffmann |
| 4,612,132 A | 9/1986 | Wollenberg et al. |
| 4,716,111 A | 12/1987 | Osband et al. |
| 4,741,900 A | 5/1988 | Alvarez et al. |
| 4,816,397 A | 3/1989 | Boss et al. |
| 4,816,567 A | 3/1989 | Cabilly et al. |
| 4,946,778 A | 8/1990 | Ladner et al. |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,331,573 A | 7/1994 | Balaji et al. |
| 5,403,484 A | 4/1995 | Ladner et al. |
| 5,427,908 A | 6/1995 | Dower et al. |
| 5,463,564 A | 10/1995 | Agrafiotis |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,573,905 A | 11/1996 | Lerner et al. |
| 5,580,717 A | 12/1996 | Dower et al. |
| 5,585,089 A | 12/1996 | Queen et al. |
| 5,658,727 A | 8/1997 | Barbas et al. |
| 5,698,426 A | 12/1997 | Huse |
| 5,733,743 A | 3/1998 | Johnson et al. |
| 5,750,753 A | 5/1998 | Kimai et al. |
| 5,780,225 A | 7/1998 | Wigler et al. |
| 5,807,715 A | 9/1998 | Morrison et al. |
| 5,821,047 A | 10/1998 | Garrand et al. |
| 5,880,972 A | 3/1999 | Horlbeck |
| 5,969,108 A | 10/1999 | McCafferty et al. |
| 7,087,733 B2 * | 8/2006 | Dai ........................ 536/23.1 |

FOREIGN PATENT DOCUMENTS

| | | |
|---|---|---|
| EP | 0 045 665 A1 | 2/1982 |
| EP | 0 239 400 A2 | 9/1987 |
| EP | 0 519 596 A1 | 12/1992 |
| EP | 0 592 106 A1 | 4/1994 |
| WO | WO 86/05807 A1 | 10/1986 |
| WO | WO 89/01036 A1 | 2/1989 |
| WO | WO 90/02809 A1 | 3/1990 |
| WO | WO 91/09967 A1 | 7/1991 |
| WO | WO 91/10737 A1 | 7/1991 |
| WO | WO 91/10741 A1 | 7/1991 |
| WO | WO 92/01047 A1 | 1/1992 |
| WO | WO 92/18619 A1 | 10/1992 |
| WO | WO 92/22324 A1 | 12/1992 |
| WO | WO 93/11236 A1 | 6/1993 |
| WO | WO 95/15982 A2 | 6/1995 |
| WO | WO 95/20401 A1 | 8/1995 |
| WO | WO 96/33735 A1 | 10/1996 |
| WO | WO 96/34096 A1 | 10/1996 |
| WO | WO 98/16654 A1 | 4/1998 |
| WO | WO 98/24893 A2 | 6/1998 |

(Continued)

OTHER PUBLICATIONS

Nyska A et al. Glutathione S-transferase pi expression in forestomach carcinogenesis process induced by gavage-administered 2,4-hexadienal in the F344 rat. Archives of Toxicology, 2001; vol. 75, No. 10, pp. 618-24.

Ames BN. Dietary carcinogens and anticarcinogens. Oxygen radicals and degenerative diseases. Science, 1983; vol. 221, No. 4617, pp. 1256-1264.

Davydov VV et al. Possible role of alteration of aldehyde's scavenger enzymes during aging. Experimental Gerontology, 2004; vol. 39, No. 1, pp. 11-16.

De Bont R & van Larebeke N. Endogenous DNA damage in humans: a review of quantitative data. Mutagenesis, 2004; vol. 19, No. 3, pp. 169-185.

Choudhary S et al. Toxicity and detoxification of lipid-derived aldehydes in cultured retinal pigmented epithelial cells. Toxicology and Applied Pharmacology, 2005; vol. 204, No. 2, pp. 122-134.

(Continued)

*Primary Examiner* — Alana Harris Dent
*Assistant Examiner* — Anne Holleran
(74) *Attorney, Agent, or Firm* — McDonnell Boehnen Hulbert & Berghoff LLP

(57) ABSTRACT

This invention provides antibodies immunologically specific for human ARL-1 (also referred to AKR1B10), a species of the aldo-keto reductase superfamily of proteins. The invention also provides methods of making and methods of using said antibodies.

72 Claims, 14 Drawing Sheets

FOREIGN PATENT DOCUMENTS

| WO | WO 98/46645 A2 | 10/1998 |
|---|---|---|
| WO | WO 98/50433 A2 | 11/1998 |
| WO | WO 03/046165 A1 | 6/2003 |

OTHER PUBLICATIONS

Schuler BD & Eder E. Development of a 32P-postlabelling method for the detection of 1,N2-propanodeoxyguanosine adducts of crotonaldehyde in vivo. Archives of Toxicology, 2000; vol. 74, No. 7, pp. 404-414.

Seaman VY et al. A sensitive method for the quantification of acrolein and other volatile carbonyls in ambient air. Analytical Chemistry, 2006; vol. 78, No. 7, pp. 2405-2412.

Uchida K et al. Protein-bound acrolein: potential markers for oxidative stress. Proceedings of the National Academy of Sciences of the United States of America, 1998; vol. 95, No. 9, pp. 4882-4887.

Hashimoto M et al. Structural basis of protein-bound endogenous aldehydes. Chemical and immunochemical characterizations of configurational isomers of a 4-hydroxy-2-nonenal-histidine adduct. The Journal of Biological Chemistry, 2003; vol. 278, No. 7, pp. 5044-5051.

Okada K et al. 4-Hydroxy-2-nonenal-mediated impairment of intracellular proteolysis during oxidative stress. Identification of proteasomes as target molecules. The Journal of Biological Chemistry, 1999; vol. 274, No. 34, pp. 23787-23793.

Uchida K et al. Selective cleavage of thioether linkage in proteins modified with 4-hydroxynonenal. Proceedings of the National Academy of Sciences of the United States of America, 1992; vol. 89, No. 12, pp. 5611-5615.

Yang IY et al. Mutagenesis by acrolein-derived propanodeoxyguanosine adducts in human cells. Biochemistry, 2002; vol. 41, No. 46, pp. 13826-13832.

Nagy E et al. DNA adduct and tumor formations in rats after intratracheal administration of the urban air pollutant 3-nitrobenzanthrone. Carcinogenesis, 2005; vol. 26, No. 10, pp. 1821-1828.

Cline SD et al. Malondialdehyde adducts in DNA arrest transcription by T7 RNA polymerase and mammalian RNA polymerase II. Proceedings of the National Academy of Sciences of the United States of America, 2004; vol. 101, No. 19, pp. 7275-7280.

Homann N. et al. Microbially produced acetaldehyde from ethanol may increase the risk of colon cancer via folate deficiency. International Journal of Cancer, 2000; vol. 86, No. 2, pp. 169-173.

Korenaga D et al. Impaired antioxidant defense system of colonic tissue and cancer development in dextran sulfate sodium-induced colitis in mice. The Journal of Surgical Research, 2002; vol. 102, No. 2, pp. 144-149.

Schaeferhenrich A et al. Human adenoma cells are highly susceptible to the genotoxic action of 4-hydroxy-2-nonenal. Mutation Research, 2003; vol. 526, No. 1-2, pp. 19-32.

Salaspuro MP. Alcohol consumption and cancer of the gastrointestinal tract. Best Practice & Research Clinical Gastroenterology, 2003; vol. 17, No. 4, pp. 679-694.

Sladek NE. Human aldehyde dehydrogenases: potential pathological, pharmacological, and toxicological impact. Journal of Biochemical and Molecular Toxicology, 2003; vol. 17, No. 1, pp. 7-23.

Coles BF & Kadluber FF. Detoxification of electrophilic compounds by glutathione S-transferase catalysis: determinants of individual response to chemical carcinogens and chemotherapeutic drugs? Biofactors, 2003; vol. 17, No. 1-4, pp. 115-130.

Sharma R et al. Antioxidant role of glutathione S-transferases: protection against oxidant toxicity and regulation of stress-mediated apoptosis. Antioxidants & Redox Signaling, 2004; vol. 6, No. 2, pp. 289-300.

Cao D et al. Identification and characterization of a novel human aldose reductase-like gene. The Journal of Biological Chemistry, 1998; vol. 273, No. 19, pp. 11429-11435.

Kohler G & Milstein C. Continuous cultures of fused cells secreting antibody of predefined specificity. Nature, 1975; vol. 256, No. 5517, pp. 495-497.

Kohler G & Milstein C. Derivation of specific antibody-producing tissue culture and tumor lines by cell fusion. European Journal of Immunology, 1976; vol. 6, No. 7, pp. 511-519.

Kohler G et al. Fusion between immunoglobulin-secreting and nonsecreting myeloma cell lines. European Journal of Immunology, 1976; vol. 6, No. 4, pp. 292-295.

Huse WD et al. Generation of a large combinatorial library of the immunoglobulin repertoire in phage lambda. Science, 1989; vol. 246, No. 4935, pp. 1275-1281.

Ward ES et al. Binding activities of a repertoire of single immunoglobulin variable domains secreted from *Escherichia coli*. Nature, 1989; vol. 341, No. 6242, pp. 544-546.

Brinkmann U et al. Phage display of disulfide-stabilized Fv fragments. Journal of Immunological Methods, 1995; vol. 182, No. 1, pp. 41-50.

Ames RS et al. Conversion of murine Fabs isolated from a combinatorial phage display library to full length immunoglobulins. Journal of Immunological Methods, 1995; vol. 184, No. 2, pp. 177-186.

Kettleborough CA et al. Isolation of tumor cell-specific single-chain Fv from immunized mice using phage-antibody libraries and the re-construction of whole antibodies from these antibody fragments. European Journal of Immunology, 1994; vol. 24, No. 4, pp. 952-958.

Mulligan RC & Berg P. Selection for animal cells that express the *Escherichia coli* gene coding for xanthine-guanine phosphoribosyltransferase. Proceedings of the National Academy of Sciences of the United States of America, 1981; vol. 78, No. 4, pp. 2072-2076.

Mulligan RC. The basic science of gene therapy. Science, 1993; vol. 260, No. 5110, pp. 926-932.

Colbere-Garapin F et al. A new dominant hybrid selective marker for higher eukaryotic cells. Journal of Molecular Biology, 1981; vol. 150, No. 1, pp. 1-14.

Crouse GF et al. Expression and amplification of engineered mouse dihydrofolate reductase minigenes. Molecular and Cellular Biology, 1983; vol. 3, No. 2, pp. 257-266.

Proudfoot NJ. Transcriptional interference and termination between duplicated alpha-globin gene constructs suggests a novel mechanism for gene regulation. Nature, 1986; vol. 322, No. 6079, pp. 562-565.

Kohler G. Immunoglobulin chain loss in hybridoma lines. Proceedings of the National Academy of Sciences of the United States of America, 1980; vol. 77, No. 4, pp. 2197-2199.

Veber DF & Freidinger RM. The design of metabolically-stable peptide analogs. Trends in Neuroscience, 1985; vol. 8, pp. 392-396.

Evans BE et al. Design of nonpeptidal ligands for a peptide receptor: cholecystokinin antagonists. Journal of Medicinal Chemistry, 1987; vol. 30, No. 7, pp. 1229-1239.

Merrifield RB. Solid Phase Peptide Synthesis. I. The Synthesis of a Tetrapeptide. Journal of the American Chemical Society, 1963; vol. 85, No. 14, pp. 2149-2154.

Carpino LA. New amino-protecting groups in organic synthesis. Accounts of Chemical Research, 1973; vol. 6, No. 6, pp. 191-198.

Kent SB. Chemical synthesis of peptides and proteins. Annual Review of Biochemistry, 1988; vol. 57, pp. 957-989.

Morley JS. Modulation of the Action of Regulatory Peptides by Structural Modification. Trends in Pharmacological Sciences; vol. 1, pp. 463-468.

Spatola AF et al. Structure-activity relationships of enkephalins containing serially replaced thiomethylene amide bond surrogates. Life Sciences, 1986; vol. 38, No. 14, pp. 1243-1249.

Hann M et al. On the double bond isostere of the peptide bond: preparation of an enkephalin analogue. Journal of the Chemical Society, Perkin Transactions 1, 1982; pp. 307-314.

Almquist RG et al. Synthesis and biological activity of a ketomethylene analogue of a tripeptide inhibitor of angiotensin converting enzyme. Journal of Medicinal Chemistry, 1980; vol. 23, No. 12, pp. 1392-1398.

Hruby VJ. Conformational restrictions of biologically active peptides via amino acid side chain groups. Life Sciences, 1982; vol. 31, No. 3, pp. 189-199.

McPherson A. Current approaches to *Macromolecular crystallization*. European Journal of Biochemistry, 1990; vol. 189, No. 1, pp. 1-23.

Gallop MA et al. Applications of combinatorial technologies to drug discovery. 1. Background and peptide combinatorial libraries. Journal of Medicinal Chemistry, 1994; vol. 37, No. 9, pp. 1233-1251.

Gordon EM et al. Applications of combinatorial technologies to drug discovery. 2. Combinatorial organic synthesis, library screening strategies, and future directions. Journal of Medicinal Chemistry, 1994; vol. 37, No. 10, pp. 1385-1401.

Ruhland B et al. Solid-Supported Combinatorial Synthesis of Structurally Diverse β-Lactams. Journal of the American Chemical Society, 1996; vol. 118, No. 1, pp. 253-254.

Thompson LA & Ellman JA. Synthesis and Applications of Small Molecule Libraries. Chemical Reviews, 1996; vol. 96, No. 1, pp. 555-600.

Fruchtel JS & Jung G. Organic Chemistry on Solid Supports. Angewandte Chemie International Edition in English, 1996; vol. 35, No. 1, pp. 17-42.

Pavia MR. The Chemical Generation of Molecular Diversity. Network Science Center, www.netsi.org, 1995.

Mjalli AM & Toyonaga BE. Solid Support Combinatorial Chemistry in Lead Discovery and SAR optimization. Network Science Center, www.netsi.org, 1995.

Davies K & Briant C. Combinatorial Chemistry Library Design Using Pharmacophere Diversity. Network Science Center, www.netsi.org, 1995.

Petrash JM. All in the family: aldose reductase and closely related aldo-keto reductases. Cellular and Molecular Life Sciences, 2004; vol. 61, No. 7-8, pp. 737-749.

Fukumoto S et al. Overexpression of the aldo-keto reductase family protein AKR1B10 is highly correlated with smokers' non-small cell lung carcinomas. Clinical Cancer Research, 2005; vol. 11, No. 5, pp. 1776-1785.

Martinet W et al. Detection of autophagy in tissue by standard immunohistochemistry: possibilities and limitations. Autophagy, 2006; vol. 2, No. 1, pp. 55-57.

Suzuki D et al. Immunohistochemical evidence for an increased oxidative stress and carbonyl modification of proteins in diabetic glomerular lesions. Journal of the American Society of Nephrology, 1999; vol. 10, No. 4, pp. 822-832.

Dake BL et al. Effect of an insulin-like growth factor binding protein fusion protein on thymidine incorporation in neuroblastoma and rhabdomyosarcoma cell lines. Endocrinology, 2004; vol. 145, No. 7, pp. 3369-3374.

Yuan J et al. Cyclin B1 depletion inhibits proliferation and induces apoptosis in human tumor cells. Oncogene, 2004; vol. 23, No. 34, pp. 5843-5852.

Koh JY & Choi DW. Quantitative determination of glutamate mediated cortical neuronal injury in cell culture by lactate dehydrogenase efflux assay. Journal of Neuroscience Methods, 1987; vol. 20, No. 1, pp. 83-90.

Li Y et al. Cleavage of lumican by membrane-type matrix metalloproteinase-1 abrogates this proteoglycan-mediated suppression of tumor cell colony formation in soft agar. Cancer Research, 2004; vol. 64, No. 19, pp. 7058-7064.

Jin JF et al. Preparation and characterization of polyclonal antibodies against ARL-1 protein. World Journal of Gastroenterology, 2003; vol. 9, No. 7, pp. 1455-1459.

Shan J et al. [Preparation and characterization of monoclonal antibody against ARL-1 protein]. Xi Bao Yu Fen Zi Mian Yi Xue Za Zhi = Chinese Journal of Cellular and Molecular Immunology, 2005; vol. 21, No. 1, pp. 60-3 (abstract).

Martin HJ et al. Purification and characterization of akr1b10 from human liver: role in carbonyl reduction of xenobiotics. Drug Metabolism and Disposition, 2006; vol. 34, No. 3, pp. 464-470.

Hyndman DJ & Flynn TG. Sequence and expression levels in human tissues of a new member of the aldo-keto reductase family. Biochimica et Biophysica Acta, 1998; vol. 1399, No. 2-3, pp. 198-202.

Persic L et al. An integrated vector system for the eukaryotic expression of antibodies or their fragments after selection from phage display libraries. Gene, 1997; vol. 187, No. 1, pp. 9-18.

Burton DR & Barbas CF. Human antibodies from combinatorial libraries. Advances in Immunology, 1994; vol. 57, pp. 191-280.

Mullinax RL et al. Expression of a heterodimeric Fab antibody protein in one cloning step. BioTechniques, 1992; vol. 12, No. 6, pp. 864-869.

Sawai H et al. Direct production of the Fab fragment derived from the sperm immobilizing antibody using polymerase chain reaction and cDNA expression vectors. AJRI, 1995; vol. 34, pp. 26-34.

Better M et al. *Escherichia coli* secretion of an active chimeric antibody fragment. Science, 1988; vol. 240, No. 4855, pp. 1041-1043.

Huston JS et al. Protein engineering of single-chain Fv analogs and fusion proteins. Methods in Enzymology, 1991; vol. 203, pp. 46-88.

Shu L et al. Secretion of a single-gene-encoded immunoglobulin from myeloma cells. Proceedings of the National Academy of Sciences of the United States of America, 1993; vol. 90, No. 17, pp. 7995-7999.

Skerra A & Pluckthun A. Assembly of a functional immunoglobulin Fv fragment in *Escherichia coli*. Science, 1988; vol. 240, No. 4855, pp. 1038-1041.

Morrison SL. Transfectomas provide novel chimeric antibodies. Science, 1985; vol. 229, No. 4719, pp. 1202-1207.

Gillies SD et al. High-level expression of chimeric antibodies using adapted cDNA variable region cassettes. Journal of Immunological Methods, 1989; vol. 125, No. 1-2, pp. 191-202.

Riechmann L et al. Reshaping human antibodies for therapy. Nature, 1988; vol. 332, No. 6162, pp. 323-327.

Padlan EA. A possible procedure for reducing the immunogenicity of antibody variable domains while preserving their ligand-binding properties. Molecular Immunology, 1991; vol. 28, No. 4-5, pp. 489-498.

Roguska MA et al. Humanization of murine monoclonal antibodies through variable domain resurfacing. Proceedings of the National Academy of Sciences of the United States of America, 1994; vol. 91, No. 3, pp. 969-973.

Jespers LS et al. Guiding the selection of human antibodies from phage display repertoires to a single epitope of an antigen. Bio/Technology, 1994; vol. 12, No. 9, pp. 899-903.

Kutmeier G et al. Assembly of humanized antibody genes from synthetic oligonucleotides using a single-round PCR. BioTechniques, 1994; vol. 17, No. 2, pp. 242-246.

Chothia C et al. Structural determinants in the sequences of immunoglobulin variable domain. Journal of Molecular Biology, 1998; vol. 278, No. 2, pp. 457-479.

Morrison SL et al. Chimeric human antibody molecules: mouse antigen-binding domains with human constant region domains. Proceedings of the National Academy of Sciences of the United States of America, 1984; vol. 81, No. 21, pp. 6851-6855.

Neuberger MS et al. Recombinant antibodies possessing novel effector functions. Nature, 1984; vol. 312, No. 5995, pp. 604-608.

Takeda S et al. Construction of chimaeric processed immunoglobulin genes containing mouse variable and human constant region sequences. Nature, 1985; vol. 314, No. 6010, pp. 452-454.

Bird RE et al. Single-chain antigen-binding proteins. Science, 1988; vol. 242, No. 4877, pp. 423-426.

Huston JS et al. Protein engineering of antibody binding sites: recovery of specific activity in an anti-digoxin single-chain Fv analogue produced in *Escherichia coli*. Proceedings of the National Academy of Sciences of the United States of America, 1988; vol. 85, No. 16, pp. 5879-5883.

Ruther U & Muller-Hill B. Easy identification of cDNA clones. The EMBO Journal, 1983; vol. 2, No. 10, pp. 1791-1794.

Inouye S & Inouye M. Up-promoter mutations in the Ipp gene of *Escherichia coli*. Nucleic Acids Research, 1985; vol. 13, No. 9, pp. 3101-3110.

Van Heeke G & Schuster SM. Expression of human asparagine synthetase in *Escherichia coli*. The Journal of Biological Chemistry, 1989; vol. 264, No. 10, pp. 5503-5509.

Logan J & Shenk T. Adenovirus tripartite leader sequence enhances translation of mRNAs late after infection. Proceedings of the National Academy of Sciences of the United States of America, 1984; vol. 81, No. 12, pp. 3655-3659.

Bitter GA et al. Expression and secretion vectors for yeast. Methods in Enzymology, 1987; vol. 153, pp. 516-544.

Szybalska EH & Szybalska W. Genetics of human cell lines, IV. DNA-mediated heritable transformation of a biochemical trait. Proceedings of the National Academy of Sciences of the United States of America, 1962; vol. 48, pp. 2026-2034.

Lowy I et al. Isolation of transforming DNA: cloning the hamster aprt gene. Cell, 1980; vol. 22, No. 3, pp. 817-823.

Wigler M et al. Transformation of mammalian cells with an amplifiable dominant-acting gene. Proceedings of the National Academy of Sciences of the United States of America, 1980; vol. 77, No. 6, pp. 3567-3570.

O'Hare K et al. Transformation of mouse fibroblasts to methotrexate resistance by a recombinant plasmid expressing a prokaryotic dihydrofolate reductase. Proceedings of the National Academy of Sciences of the United States of America, 1981; vol. 78, No. 3, pp. 1527-1531.

Pavia M.R. Chemically Generated Screening Libraries: Present and Future. Network Science Center, www.netsi.org.1996.

* cited by examiner

Figure 1A
AKR1B10 Antibody Specificity
1A1  1B1  1B10  1C1  1C2  1C3  1C4
1:1000 1° *anti*-AKR1B10
1:1000 2° *anti*-rabbit IgG
2 µg recombinant protein
1A1  1B1  1B10  1C1  1C2  1C3  1C4
1:1000 1° *anti*-AKR1B10
1:1000 2° *anti*-mouse IgG
2 µg recombinant protein
1A1  1B1  1B10  1C1  1C2  1C3  1C4
1:1000 1° *anti*-1B10
1:1000 2° *anti*-rabbit IgG
2 µg recombinant protein

ACTIVITY AND SPECIFICITY OF AKR1B10 ANTIBODY
FIG. 1B) Activity and specificity of AKR1B10 and AR antibodies
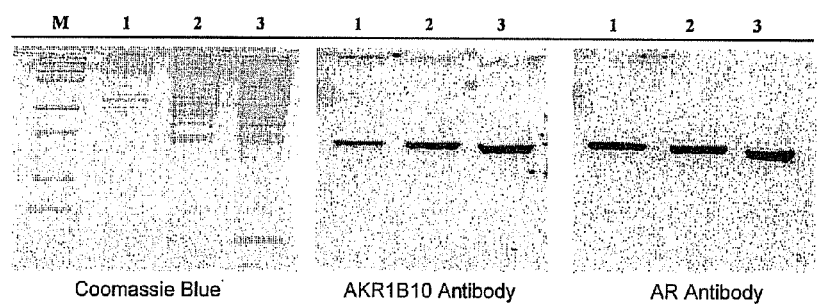
FIG. 1C) Cross-reactivity of AKR1B10 and AR antibodies
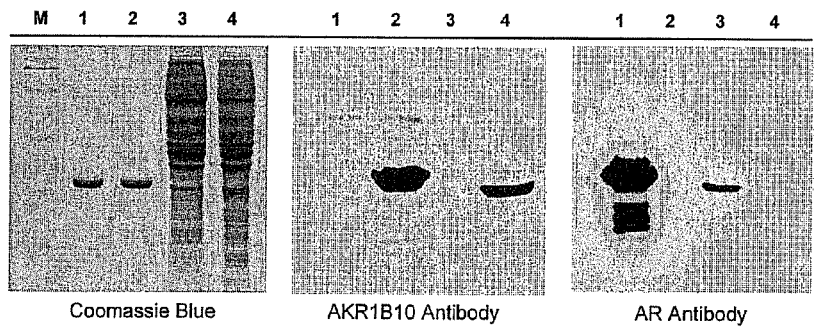

Figures 2A and 2B Cellular distribution of ARL-1 protein in normal column tissues
2A
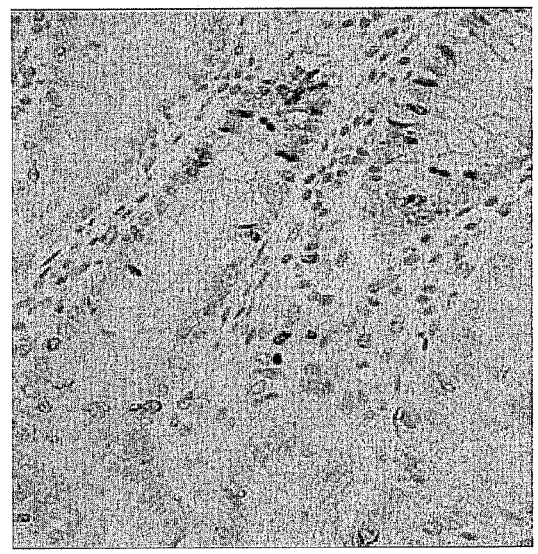
2B

SEQUENCE LISTING

```
<160> NUMBER OF SEQ ID NOS: 3

<210> SEQ ID NO 1
<211> LENGTH: 15
<212> TYPE: PRT
<213> ORGANISM: Artificial
<220> FEATURE:
<223> OTHER INFORMATION: Synthetic; Peptide used as specific antigen
      to raise anti-ARL-1 antibodies

<400> SEQUENCE: 1

Asp Asp Lys Gly Asn Ala Ile Gly Gly Lys Ala Thr Phe Leu Cys
1               5                   10                  15

<210> SEQ ID NO 2
<211> LENGTH: 21
<212> TYPE: DNA
<213> ORGANISM: Artificial
<220> FEATURE:
<223> OTHER INFORMATION: Synthetic; siRNA targeted to encoding region
      of ARL-1
<220> FEATURE:
<221> NAME/KEY: misc_feature
<222> LOCATION: (1)..(19)
<223> OTHER INFORMATION: ribonucleotide as described

<400> SEQUENCE: 2
gcaaguugug gcccacuuut t                                              21

<210> SEQ ID NO 3
<211> LENGTH: 21
<212> TYPE: DNA
```

-continued

```
<213> ORGANISM: Artificial
<220> FEATURE:
<223> OTHER INFORMATION: Synthetic; siRNA targeted to 3' untranslated
      region of ARL-1
<220> FEATURE:
<221> NAME/KEY: misc_feature
<222> LOCATION: (1)..(19)
<223> OTHER INFORMATION: ribonucleotide as described

<400> SEQUENCE: 3
cgagaaucga ggugcuguut                                                    21
```

ARL-1 SPECIFIC ANTIBODIES

This application claims priority to U.S. provisional patent application Ser. No. 60/890,414, filed Feb. 16, 2007, the disclosure of which is expressly incorporated by reference herein in its entirety.

The invention was made with government support under grant number CA122327 awarded by the National Institutes of Health. The government has certain rights in this invention.

BACKGROUND OF THE INVENTION

1. Field of the Invention

This invention relates to antibodies specific for proteins differentially expressed in normal and tumor or precancerous cells and tissues. The invention more specifically relates to antibodies that are immunologically specific for a particular human protein, ARL-1 (also referred to as AKR1B10), a species of protein in the aldo-keto reductase (AKR) superfamily. The invention particularly relates to polyclonal antisera, monoclonal antibodies and fragments and derivatives thereof that are immunologically specific for ARL-1 differentially expressed in normal and tumor or precancerous cells and tissues of the gastrointestinal tract. Methods for making and using said antibodies are also provided.

2. Summary of the Related Art

Cancer remains one of the leading causes of death in the United States, with colon cancer representing the second leading cause of cancer death in the U.S. (Nyska et al., 2001, *Arch Toxicol.* 75: 618-624). It has long been recognized that development of cancer, particularly cancers that occur in later life such as colon cancer, are in part the result of lifelong exposure to environmental carcinogens. Surprisingly, many of these carcinogens are contained in or produced from foods and other natural products. See, Ames, 1983, *Science* 221: 1256-1264

For example, electrophilic carbonyls are constantly produced during metabolism of carbohydrate and lipid (Davydov et al., 2004, *Exp Gerontol.* 39: 11-16; De Bont & van Larebeke, 2004, *Mutagenesis* 19: 169-185; Choudhary et al., 2005, *Toxicol Appl Pharmacol.* 204: 122-134, 2005). Carbonyls also widely exist in air, water, and various foodstuffs and beverages (Bowmer & Higgins, 1976, *Arch Environ Contam Toxicol.* 5: 87-96; Schuler & Eder, 2000, *Arch Toxicol.* 74: 404-414; Seaman et al., 2006, *Anal Chem.* 78: 2405-2412). Human exposure to carbonyls occurs in consumption of fruits, vegetables, fish, meat, and alcoholic beverages, such as wine and whisky (Bowmer & Higgins, 1976, Id; Uchida et al., 1998, *Proc Natl Acad Sci USA* 95: 4882-4887). Indeed, carcinogenic methylglyoxal is a constituent of daily consumed coffee, whereas carcinogenic crotonaldehyde is widely present in fruit (5.4-78 µg/kg), vegetables (1.4-100 µg/kg), fish (71.4-1000 µg/kg), meat (10-270 µg/kg), and alcoholic beverages, such as wine (300-700 µg/L) and whisky (30-210 µg/L) (Schuler et al., 2000, *Arch Toxicol.* 74: 404-414.).

Because of their reactivity, carbonyls can interact with free amino and sulfhydryl groups of proteins, peptides and amino acids, forming covalently modified adducts (Davydov et al., 2004, Id.; Vasiliou et al., 2000, *Chem Biol Interact.* 129: 1-19; Hashimoto et al., 2003, *J Biol Chem.* 278: 5044-5051; Okada et al., 1999, *J Biol Chem.* 274: 23787-23793; Uchida et al., 1992, *Proc Natl Acad Sci USA*, 89: 5611-5615). These nonspecific, covalent modifications may cause protein dysfunction, resistance to intracellular proteolysis, or depolymerization. Protein adducts may also act as secondary messengers, autoantigens, or inhibitors of proteosomes, causing cellular damage and/or autoimmune disorders.

Electrophilic carbonyls can also react with nucleic acids (DNA), forming covalently modified DNA adducts. DNA adducts can block DNA semiconservative replication performed by DNA polymerase, arrest transcription driven by RNA polymerase, and cause DNA mutations and breaks (De Bont & van Larebeke, 2004, Id.; Yang et al., 2002, *Biochemistry* 41: 13826-13832; Hou et al., 1995, *Environ Mol Mutagen* 26: 286-291; Nagy et al., 2005, *Carcinogenesis* 26: 1821-1828; Cline et al., 2004, *Proc Natl Acad Sci USA* 101: 7275-7280, 2004). Documented evidence has indicated the pathogenic effect of carbonyl-derived DNA modifications, resulting in mutagenesis, carcinogenesis, and other age-related diseases (Davydov et al., 2004, Id.; Yang et al., 2002, *Biochemistry* 41: 13826-13832; Nagy et al., 2005, *Carcinogenesis* 26: 1821-1828; Ames, 1983, Id.).

Consequently, electrophilic dietary carbonyls are important pathogens of gastrointestinal (GI) diseases, including neoplasms (Homann et al., 2000, *Int J Cancer* 86: 169-173; Nyska et al., 2001, Id.; Korenaga et al., 2002, *J Surg Res* 102: 144-149; Schaeferhenrich et al., 2003, *Mutat Res.* 526: 19-32). Via food consumption, GI cells are repeatedly exposed to various reactive carbonyls (Ames, 1983, Id.: Fujioka & Shibamoto, 2004, *Lipids* 39: 481-486, 2004). This long term and cumulative carbonyl exposure, even though minimal, may eventually cause carcinogenic changes of GI cells. Indeed, exposure of F344 rats to 2,4-hexadienal induced stomach hyperplasia, squamous papilloma, and carcinoma in rats; and high levels of malondialdehyde (MDA) in colonic mucosa was pathogenically related to neoplastic lesions in ulcerative colitis (Korenaga et al., 2002, Id.; Nyska et al., 2001, Id.). In addition, local accumulation of acetaldehyde, microbially produced after alcohol consumption, has been considered a carcinogenic factor for colon and gastric cancers (Homann et al., 2000, Id.; Salaspuro, 2003, *Best Pract Res Clin Gastroenterol.* 17: 679-694).

Nevertheless, little is known of the GI-specific protective mechanisms against carcinogenic lesions induced by dietary carbonyls. Aldehyde dehydrogenase and glutathione-S-transferase (GST) are important enzymes in elimination of intracellular carbonyls by catalyzing carbonyl oxidation to carbonic acids or conjugation with glutathione, but no evidence demonstrates their GI-specificity (Vasiliou et al., 2000, Id.; Sladek, 2003, *J Biochem Mol Toxicol.* 17: 7-23; Coles & Kadlubar, 2003, *Biofactors* 17: 115-130; Sharma et al., 2004, *Antioxid Redox Signal.* 6: 289-300, 2004).

There is a need in this art to identify endogenous protective mechanisms and proteins involved in such mechanisms. There is further a need in this art to identify whether differential expression of proteins involved in protecting gastrointestinal cells and tissues from the mutagenic and carcinogenic effects of food-related reactive carbonyls provides a marker for cells and tissues at risk for neoplastic transformation and tumor formation, or identifies cells having resistance to anticancer chemotherapeutic drugs, or provides a target for therapeutic and prevention interventions in cancer or precancerous states.

SUMMARY OF THE INVENTION

This invention provides an antibody that specifically binds to human ARL-1 protein, also referred to as AKR1B10. In certain embodiments, the antibody comprises a polyclonal antisera. In alternative embodiments, the antibody is a monoclonal antibody. The antibodies of the invention specifically bind to an epitope defined by an amino acid sequence identified by SEQ ID NO: 1. Antibodies of the invention are advantageously produced by immunizing an animal with a peptide having the amino acid sequence is identified by SEQ ID NO: 1. The invention provides methods for detecting human ARL-1 protein comprising the steps of contacting a sample comprising human ARL-1 protein with an antibody of claim 1 and detecting binding of the antibody with the protein.

ARL-1 expression can be detected, particularly in human gastrointestinal tissues using the antibodies of the invention, particularly in liver, lung, stomach, small intestine or colon. Thus, the invention provides methods for detecting ARL-1 protein in a tissue sample, particularly a liver, lung, stomach, small intestine or colon tissue sample. ARL-1 protein is detected using methods including in situ immunohistochemistry and Western blot analysis.

This invention also provides diagnostic and prognostic methods for identifying individuals with gastrointestinal cancer or precancerous conditions wherein neoplastic or preneoplastic cells therein show differential expression of ARL-1. As set forth herein, ARL-1 protein is differentially expressed in normal colon, precancerous lesions and colon cancer. In certain embodiments, cancer or precancerous conditions affect the stomach, small intestine or colon and show a loss of ARL-1 expression. In other embodiments, the cancer or precancerous conditions affect the liver and show increased ARL-1 expression. In yet other embodiments, cancer or precancerous conditions affect the lungs and show increased ARL-1 expression.

Hence the invention provides methods for identifying colon cancer or precancerous lesions of the colon, comprising the step of identifying expression of ARL-1 protein in a normal colon epithelium sample and in a colon cancer sample or precancerous lesion sample from a human using an antibody of the invention, wherein cancer or precancerous lesion is identified when ARL-1 expression is lower in the cancer or precancerous lesion than in the normal colon epithelium sample. In certain embodiments, ARL-1 expression is detected by in situ immunohistochemistry. In other embodiments, ARL-1 expression is detected by Western blot analysis.

The invention also provides methods for detecting a precancerous lesion in a human gastrointestinal tract sample, comprising the step of identifying expression of ARL-1 protein in a normal human gastrointestinal tract sample and in a precancerous lesion sample from a human using an antibody of the invention, wherein a precancerous lesion is identified when ARL-1 expression is lower in the precancerous lesion than in the human gastrointestinal tract sample. In certain embodiments, ARL-1 expression is detected by in situ immunohistochemistry. In other embodiments, ARL-1 expression is detected by Western blot analysis.

The invention also provides methods for identifying a human having colon cancer or a precancerous lesion in normal colon epithelium sample from the human and in a colon cancer sample or precancerous lesion sample from the human using an antibody of the invention, wherein a precancerous lesion is identified when ARL-1 expression is lower in the precancerous lesion than in the human gastrointestinal tract sample. In certain embodiments, ARL-1 expression is detected by in situ immunohistochemistry. In other embodiments, ARL-1 expression is detected by Western blot analysis.

The invention also provides methods for identifying a human having breast cancer at early stage or a precancerous lesion in normal breast epithelium sample from the human and in a breast cancer sample or precancerous lesion sample from the human using an antibody of the invention, wherein breast cancer or a precancerous lesion is identified when ARL-1 expression is higher in the tumor or precancerous lesion than in non-cancerous human breast tissue. In certain embodiments, ARL-1 expression is detected by in situ immunohistochemistry. In other embodiments, ARL-1 expression is detected by Western blot analysis.

The invention also provides methods for identifying a human at risk for developing a gastrointestinal cancer, comprising the step of identifying expression of ARL-1 protein in a histologically-normal human gastrointestinal tract sample and in a precancerous lesion sample from a human using an antibody of the invention, wherein a individual at high risk for developing a gastrointestinal cancer is identified when ARL-1 expression is lost or lower in the histologically-normal colon epithelium sample. In certain embodiments, ARL-1 expression is detected by in situ immunohistochemistry. In other embodiments, ARL-1 expression is detected by Western blot analysis.

The invention also provides methods for identifying a human at risk for developing breast cancer using an antibody of the invention, by identifying increased expression of ARL-1 protein in a sample of histologically-normal human breast tissue. In certain embodiments, ARL-1 expression is detected by in situ immunohistochemistry. In other embodiments, ARL-1 expression is detected by Western blot analysis.

ARL-1 expression can also be assayed by detecting mRNA. Thus, the invention provides methods for identifying colon cancer or precancerous lesions of the colon, comprising the step of identifying expression of ARL-1 mRNA in a normal colon epithelium sample and in a colon cancer sample or precancerous lesion sample from a human, wherein cancer or precancerous lesion is identified when ARL-1 expression is lower in the cancer or precancerous lesion than in the normal colon epithelium sample. In certain embodiments, ARL-1 mRNA is detected by in situ hybridization. In other embodiments, ARL-1 mRNA is detected by in vitro amplification, particularly polymerase chain reaction (PCR) and more particularly by reverse transcription-polymerase chain reaction (RT-PCR).

Thus, the invention also provides methods for detecting a precancerous lesion in a human gastrointestinal tract sample, comprising the step of identifying expression of ARL-1 mRNA in a normal human gastrointestinal tract sample and in a precancerous lesion sample from a human, wherein a precancerous lesion is identified when ARL-1 expression is lower in the precancerous lesion than in the human gastrointestinal tract sample. In certain embodiments, ARL-1 mRNA is detected by in situ hybridization. In other embodiments, ARL-1 mRNA is detected by in vitro amplification, particularly PCR and more particularly by RT-PCR.

The invention further provides methods for identifying a human with colon cancer or precancerous lesions of the colon, comprising the step of identifying expression of ARL-1 mRNA in a normal colon epithelium sample from the human and in a colon cancer sample or precancerous lesion sample from the human, wherein cancer or precancerous lesion is identified when ARL-1 expression is lower in the cancer or precancerous lesion than in the normal colon epithelium sample. In certain embodiments, ARL-1 mRNA is detected by in situ hybridization. In other embodiments, ARL-1 mRNA is detected by in vitro amplification, particularly PCR and more particularly by RT-PCR.

The invention also provides methods for identifying a human at risk for developing a gastrointestinal cancer, comprising the step of identifying expression of ARL-1 mRNA in a histologically-normal human gastrointestinal tract sample and in a precancerous lesion sample from a human, wherein a individual at high risk for developing a gastrointestinal cancer is identified when ARL-1 expression is lost or lower in the histologically-normal colon epithelium sample. In certain embodiments, ARL-1 mRNA is detected by in situ hybridization. In other embodiments, ARL-1 mRNA is detected by in vitro amplification, particularly PCR and more particularly by RT-PCR.

The invention provides methods for identifying a human with breast cancer or precancerous lesions of breast epithelia, or a human at risk for developing breast cancer, comprising the step of identifying increased expression of ARL-1 mRNA in a tumor sample or histologically-normal breast tissue. In certain embodiments, ARL-1 mRNA is detected by in situ hybridization. In other embodiments, ARL-1 mRNA is detected by in vitro amplification, particularly polymerase chain reaction (PCR) and more particularly by reverse transcription-polymerase chain reaction (RT-PCR).

The invention yet further provides methods for detecting expression of human ARL-1 mRNA comprising the steps of hybridizing a nucleic acid sample comprising ARL-1 mRNA with a nucleic acid probe encoding the amino acid identified by SEQ ID NO: 1. In certain embodiments, ARL-1 mRNA is detected by in situ hybridization. In other embodiments, ARL-1 mRNA is detected by in vitro amplification, particularly PCR and more particularly by RT-PCR.

The invention also provides a kit for the practice of the diagnostic and prognostic methods of the invention, comprising a preparation of the antibodies of the invention and instructions for use. In certain embodiments, the kits also contain reagents, such as reagents for in situ hybridization, useful in the practice of the methods of the invention.

Specific preferred embodiments of the present invention will become evident from the following more detailed description of certain preferred embodiments and the claims.

BRIEF DESCRIPTION OF THE DRAWINGS

FIG. 1A shows the results of Western blot analysis of several members of the aldo-keto reductase (AKR) superfamily detected using the polyclonal antisera of this invention and two alternative antibody preparations. 2.0 μg of purified protein were electrophoresed per lane.

FIG. 1B shows the results of Coomassie blue staining and Western blot analysis of cell lysates from increasing numbers (Lane 2: 10,000; Lane 3: 50,000; Lane 4: 100,000) of A549 cells, which express both AR and ARL-1 (AKR1B10); Lane M contains size marker. Western blots are probed with anti-AR antibodies and anti-ARL-1 antibodies according to the invention.

FIG. 1C shows the results of Western blot analysis of purified AR (Lane 1) and ARL-1 (AKR1B10; Lane 2) protein probed with AR and ARL-1 (AKR1B10) antibodies; also shown are whole cell lysates from 293T cells (that express AR; Lane 3) and HCT-8 cells (that express ARL-1; Lane 4). Lane M contains size marker.

FIGS. 2A and 2B are photomicrographs (20× objective) showing ARL-1 expression in normal colon. Adjacent paraffin sections of a normal colon tissue were assayed by immunohistochemistry as described in Example 3. FIG. 2A demonstrates that the ARL-1 protein is specifically expressed in mature epithelial cells of the colon, as indicated by Ki-67, a protein marker of proliferating cells shown in FIG. 2B. Ki-67 positive cells are mainly located in the crypts.

FIG. 7B), and thymidine incorporation assessment (FIG. 7D). Cells for growth rate assays were collected by trypsinization at indicated time points and viable cells were counted by trypan blue staining. Western blot, enzymatic activity, and thymidine incorporation into DNA were performed 72 hours after siRNA delivery. For thymidine incorporation, HCT-8 cells were pulsed with [$^3$H]-thymidine for 2 hours before harvest with rubber policeman. Acidic insoluble nucleic acids were precipitated by 15% trichloroacetic acid and the radioactivity was measured by scintillation counter and corrected with protein amounts. All values represent mean±SD from three independent measurements. * denotes statistical significance ($P<0.05$ or $P<0.01$, if two asterisks), compared to control.

DETAILED DESCRIPTION OF THE PREFERRED EMBODIMENTS

Figure 3:
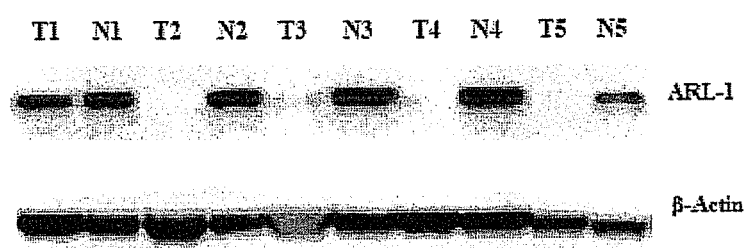
FIG. 3 is a photomicrograph of Western blot analysis of ARL-1 protein in normal and colon cancer samples. Soluble proteins (50 μg each) isolated from normal and cancer colon tissues were used for Western blot using ARL-1 specific antibody of the invention. ARL-1 protein was not detectable in Tumor 2, 4 and 5 and dramatically reduced in Tumor 3. T, tumor; N, Normal.

This invention provides antibodies, including polyclonal antisera, monoclonal antibodies and fragments and derivatives thereof, that are immunologically specific for a particular member of the aldo-keto reductase (AKR) superfamily of proteins. This member, aldose reductase-like-1 (ARL-1, also designated aldo-keto reductase family 1 B10, AKR1B10) is a protein recently identified by the inventor that is overexpressed in hepatocellular carcinoma (Cao et al., 1998, *J Biol. Chem.* 273: 11429-11435, 1998). When expressed recombinantly, this protein showed strong enzymatic activity with a range of carbonyls. As shown herein, the expression and cellular distribution of ARL-1 protein in the gastrointestinal tract, an organ with high frequency of malignant disease, and its enzymatic activity and kinetic constants in relation to acrolein and crotonaldehyde, two highly mutagenic and carcinogenic carbonyls with wide dietary distributions, indicated that ARL-1 is a marker for gastrointestinal cancer cells and precancer cells. These results were supported further by the effect of cellular ARL-1 activity on cell viability, clonogenic growth, and response to extra carbonyl stress. The results disclosed herein showed that ARL-1 is an important protein that protects gastrointestinal cells from dietary carbonyl carcinogenic lesions and a marker for gastrointestinal precancerous and cancer cells, and cells resistant to certain anticancer chemotherapeutic drugs.

The ARL-1 protein is related by amino acid sequence to other members of the aldo-keto reductase (AKR) superfamily of proteins. Despite the close sequence relationship between the members of this superfamily of proteins (Cao et al., 1998, Id.), the inventor has found a peptide antigen derived from the ARL-1 amino acid sequence capable of being used to produce antibodies as defined herein having specificity for ARL-1 and that do not cross-react with other members of the superfamily. This peptide antigen is identified by the sequence:

DDKGNAIGGKATFLC.    (SEQ ID NO. 1)

It will be understood in the art that this peptide forms an epitope that is recognized by said immunologically-specific antibodies of the invention, wherein the peptide epitope is in a configuration that is sufficiently structurally equivalent to the configuration of this amino acid sequence in the native ARL-1 protein. The immunological specificity of antibodies of this invention is shown, inter alia, in FIG. 1 as described in more detail herein. As used herein, the term "immunologically specific" is intended to mean that the antibodies of this invention specifically bind to the ARL-1 species of protein without significantly detectable cross-reactivity to any other species of the AKR superfamily that are expressed in gastrointestinal and other tissues.

Antibodies of the invention can be produced by any method known in the art for the synthesis of antibodies, including chemical synthesis or recombinant expression techniques, or preferably using conventional immunological methods. As used herein, the term "antibody" includes, but is not limited to, both naturally occurring and non-naturally occurring antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. More specifically, the term "antibody" includes polyclonal and monoclonal antibodies, and antigen-binding fragments thereof such as Fab, Fab', and F(ab')$_2$ fragments. Furthermore, the term "antibody" includes chimeric antibodies and wholly synthetic antibodies, including genetically engineered antibodies, and fragments thereof. The polyclonal and monoclonal antibodies may be "purified" which means the polyclonal and monoclonal antibodies are free of any other antibodies.

The epitope peptide disclosed herein is advantageously used to prepare antibodies that specifically bind to ARL-1 species of the AKR protein family. Antibodies are defined to be specifically binding if they bind ARL-1 with a $K_a$ of greater than or equal to $10^7$/M. The affinity of a monoclonal antibody can be readily determined by one of ordinary skill in the art (see, for example, ANTIBODIES: A LABORATORY MANUAL, Harlow and Lane (eds.), Cold Spring Harbor Laboratory Press, 1988).

Methods for preparing polyclonal and monoclonal antibodies are well known in the art (see for example, Sambrook et al., 1989, MOLECULAR CLONING: A LABORATORY MANUAL, Second Edition, Cold Spring Harbor, N.Y.; and Hurrell (Ed.), MONOCLONAL HYBRIDOMA ANTIBODIES: TECHNIQUES AND APPLICATIONS, CRC Press, Inc., Boca Raton, Fla., 1982, which are incorporated herein by reference). As would be evident to one of ordinary skill in the art, polyclonal antibodies can be generated from a variety of warm-blooded animals such as horses, cows, goats, sheep, dogs, chickens, rabbits, mice, and rats. The immunogenicity of an ARL-1 epitope peptide as disclosed herein can be increased through the use of an adjuvant such as Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. Information concerning adjuvants and various aspects of immunoassays are disclosed, for example, in Tijssen (1987, PRACTICE AND THEORY OF ENZYME IMMUNOASSAYS, 3rd Ed., Elsevier: New York). Other useful references covering methods for preparing polyclonal antisera include MICROBIOLOGY (1969, Hoeber Medical Division, Harper and Row); Landsteiner (1962, SPECIFICITY OF SEROLOGICAL REACTIONS, Dover Publications: New York), and Williams et al. (1967, METHODS IN IMMUNOLOGY AND IMMUNOCHEMISTRY, Vol. 1, Academic Press: New York).

As is well known in the art, a given composition may vary in its immunogenicity. Peptide antigen fragments may be joined to other materials, particularly polypeptides, as fused or covalently joined polypeptides to be used as immunogens. An antigen and its fragments may be fused or covalently linked to a variety of immunogens, such as keyhole limpet hemocyanin (KLH), bovine serum albumin (BSA) and other albumins such as ovalbumin, mouse serum albumin or rabbit serum albumin, tetanus toxoid, etc. Means for conjugating a polypeptide to a carrier protein are well known in the art and include glutaraldehyde, m-maleimidobenzoyl-N-hydroxysuccinimide ester, carbodiimide and bis-biazotized benzidine. See Microbiology, Hoeber Medical Division, Harper and Row, 1969; Landsteiner, 1962, Specificity of Serological Reactions, Dover Publications, New York; Williams et al., 1967, Methods in Immunology and Immunochemistry, vol. 1, Academic Press, New York; and Harlow and Lane, 1988, Id., for descriptions of methods of preparing polyclonal antisera.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored.

Serum produced from animals immunized using standard methods can be used directly, or the IgG fraction can be separated from the serum using standard methods such as plasmaphoresis or adsorption chromatography with IgG-specific adsorbents such as immobilized Protein A.

Antibody fragments, such $F(ab')_2$ and Fab fragments, can be produced from the corresponding antibodies by cleavage of and collection of the desired fragments in accordance with known methods (see, for example, Andrew et al., 1992, "Fragmentation of Immunoglobulins" in CURRENT PROTOCOLS IN IMMUNOLOGY, Unit 2.8, Greene Publishing Assoc. and John Wiley & Sons).

A variety of assays known to those skilled in the art can be utilized to detect antibodies which specifically bind to an ARL-1 epitope peptide of this invention. Exemplary assays are described in detail in Harlow & Lane (1988, Id.). Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

Alternatively, monoclonal antibodies against the antigenic peptides of the invention can be prepared according to wellknown techniques, such as those exemplified in U.S. Pat. No. 4,196,265, incorporated herein by reference. Hybridomas producing monoclonal antibodies against the antigenic peptides of the invention are produced by well-known techniques. Usually, the process involves the fusion of an immortalizing cell line with a B-lymphocyte that produces the desired antibody. Immortalizing cell lines are usually transformed mammalian cells, particularly myeloma cells of rodent, bovine, and human origin. Rodents such as mice and rats are preferred animals, however, the use of rabbit or sheep cells is also possible. Mice are preferred, with the BALB/c mouse being most preferred as this is most routinely used and generally gives a higher percentage of stable fusions.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen, and the animal is permitted to generate the desired antibody-producing cells before they are harvested for fusion with the immortalizing cell line. Most frequently, immortalized cell lines are rat or mouse myeloma cell lines that are employed as a matter of convenience and availability. Techniques for fusion are also well known in the art, and in general involve mixing the cells with a fusing agent, such as polyethylene glycol.

Generally, following immunization somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately fifty million to two hundred million lymphocytes.

Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art. Available murine myeloma lines, such as those from the American Type Culture Collection (ATCC), 10801 University Boulevard, Manassas, Va. 20110-2209, USA, may be used in the hybridization. For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XXO Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler et al., 1975, *Nature* 256:495; Kohler et al., 1976, *Eur.*

J. Immunol. 6:511; Kohler et al., 1976, Eur. J. Immunol. 6:292), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. The preferred selection medium is HAT. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

Culturing the fusion products under these conditions provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. Hybridomas secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques (such as Tijssen, 1985, Id.). The assay should be sensitive, simple and rapid, such as radioimmunoassay, enzyme immunoassays, cytotoxicity assays, plaque assays, dot immunobinding assays, and the like.

The selected hybridomas are then serially diluted and cloned into individual antibody-producing cell lines, which clones can then be propagated indefinitely to provide mAbs. The cell lines may be exploited for mAb production in at least two ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

Many references are available to provide guidance in applying the above techniques, including Kohler et al. (1980, Hybridoma Techniques, Cold Spring Harbor Laboratory, New York); Tijssen (1985, Id.); Campbell (1984, Monoclonal Antibody Technology, Elsevier: Amsterdam); Hurrell (1982, Id.). Monoclonal antibodies can also be produced using well known phage library systems. See, for example, Huse et al. (1989, Science 246:1275); Ward et al. (1989, Nature 341: 544).

Antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, $F_v$ or disulfide stabilized $F_v$ antibody domains recombinantly fused to either the phage gene III or gene VIII protein.

Examples of phage display methods that can be used to make the antibodies of the present invention include those disclosed in Brinkman et al. (1995, J. Immunol. Methods 182:41-50); Ames et al. (1995, J. Immunol. Meth. 184:177-186); Kettleborough et al. (1994, Eur. J. Immunol. 24:952-958); Persic et al. (1997, Gene 187:9-18); Burton et al. (1994, Adv. Immunol. 57:191-280); PCT application No. PCT/GB91/01134; PCT publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria. For example, techniques to recombinantly produce Fab, Fab' and $F(ab')_2$ fragments can also be employed using methods known in the art such as those disclosed in PCT publication WO 92/22324; Mullinax et al. (1992, BioTechniques 12:864-869); Sawai et al. (1995, AJRI 34:26-34); and Better et al. (1988, Science 240:1041-1043), said references incorporated by reference in their entireties.

Examples of techniques which can be used to produce single-chain $F_v$s and antibodies include those described in U.S. Pat. Nos. 4,946,778 and 5,258,498; Huston et al. (1991, Methods in Enzymology 203:46-88); Shu et al. (1993, Proc. Natl. Acad. Sci. USA 90:7995-7999); and Skerra et al. (1998, Science 240:1038-1040). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison (1985, Science 229:1202); Oi et al. (1986, BioTechniques 4:214); Gillies et al. (1989, J. Immunol. Methods 125:199-202); U.S. Pat. Nos. 5,807,715; 4,816,567; and 4,816,397, which are incorporated herein by reference in their entirety.

Humanized antibodies are antibody molecules from non-human species antibody that binds the desired antigen having one or more complementarity determining regions (CDRs)

from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, for example, U.S. Pat. No. 5,585,089, and Riechmann et al., 1988, *Nature* 332:323, which are incorporated herein by reference in their entireties.) Antibodies can be humanized using a variety of techniques known in the art including, for example, CR-grafting (European Patent Application, Publication No. EP239400; PCT publication No. WO 91/09967; U.S. Pat. Nos. 5,225,539; 5,530,101; and 5,585,089), veneering or resurfacing (European Patent Applications, Publication Nos. EP592106; EP519596; Padlan, 1991, *Molecular Immunology* 28:489 498; Studnicka et al., 1994, *Protein Engineering* 7: 805 814; Roguska et al., 1994, *Proc. Natl. Acad. Sci. USA* 91:969-973), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications Nos. WO 98/46645, WO 98/50433, WO 98/24893, WO 98/16654, WO 96/34096, WO 96/33735, and WO 91/10741; each of which is incorporated herein by reference in its entirety. Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1988, *Biotechnology* 12:899-903).

The invention further provides polynucleotides comprising a nucleotide sequence encoding an antibody of the invention and fragments thereof. The invention also encompasses polynucleotides that hybridize under stringent hybridization conditions to polynucleotides that encode an antibody, preferably, that specifically binds to a polypeptide of the invention, preferably, an antibody that binds to a peptide having the amino acid sequence of SEQ ID NO:1.

The polynucleotides may be obtained, and the nucleotide sequence of the polynucleotides determined, by any method known in the art. For example, if the amino acid or nucleotide sequence of the antibody is known, a polynucleotide encoding the antibody may be assembled from chemically synthesized oligonucleotides (such as described in Kutmeier et al., 1994, BioTechniques 17:242). Alternatively, a polynucleotide encoding an antibody may be generated from nucleic acid from a suitable source, such as a hybridoma that expresses said antibody. In the embodiments, the polynucleotide can be obtained from the cellular source using conventional methods, such as from a cDNA library or by PCR amplification of reverse-transcriptase (RT)-treated hybridoma cellular mRNA using synthetic primers that hybridize to the 3' and 5' ends of the sequence. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Id. and Ausubel et al., eds., 1998, CURRENT PROTOCOLS IN MOLECULAR BIOLOGY, John Wiley & Sons, NY, which are both incorporated by reference herein in their entireties), to generate antibodies having a different amino acid sequence, for example to create amino acid substitutions, deletions, and/or insertions.

In specific embodiments, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described in the art. The framework regions may be naturally occurring or consensus framework regions, and preferably human framework regions (see, for example, Chothia et al., 1998, *J. Mol. Biol.* 278: 457-479 for a listing of human framework regions). Preferably, the polynucleotide generated by the combination of the framework regions and CDRs encodes an antibody that specifically binds a polypeptide of the invention. Preferably, as discussed herein, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, *Proc. Natl. Acad. Sci. USA* 81:851-855; Neuberger et al., 1984, *Nature* 312:604-608; Takeda et al., 1985, *Nature* 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, *Science* 242:423-42; Huston et al., 1988, *Proc. Natl. Acad. Sci. USA* 85:5879 5883; and Ward et al., 1989, *Nature* 334: 544-54) can be adapted to produce single chain antibodies. Single chain antibodies are formed by linking the heavy and light chain fragments of the $F_v$ region via an amino acid bridge, resulting in a single chain polypeptide. Techniques for the assembly of functional $F_v$ fragments in *E. coli* may also be used (Skerra et al., 1988, *Science* 242:1038 1041).

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein.

Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, for example, PCT Publication Nos. WO86/05807, WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed herein.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

Preferably, bacterial cells such as *E. coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45: 101; Cockett et al., 1990, *Bio/Technology* 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109 (1985); Van Heeke & Schuster, *J. Biol. Chem.* 24:5503-5509); and the like. pGEX vectors (Stratagene, LaJolla, Calif.) may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems maybe utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (See, for example, Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, and other elements (see Bittner et al., 1987, *Methods in Enzymol.* 153:515-44).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter and enhancer sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, *Cell* 11:223), hypoxanthine-guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:817) genes can be employed in TK–, HGPRT– or APRT– cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78:1527; gpt, which confers resistance to mycophenolic acid (Mulligan & Berg, 1981, *Proc. Natl. Acad. Sci. USA* 78:2072; neo, which confers resistance to the aminoglycoside G-418 (Mulligan, 1993, *Science* 260:926-932; and hyg, which confers resistance to hygromycin (Santerre et al., 1984, *Gene* 30:147. Methods commonly known in the art of recombinant DNA technology may be routinely applied to select the desired recombinant clone, and such methods are described, for example, in Ausubel et al. (eds.), 1993, Id.; Kriegler, 1990, GENE TRANSFER AND EXPRESSION, A LABORATORY MANUAL, Stockton Press, NY; and Colberre-Garapin et al., 1981, *J. Mol. Biol.* 150:1, which are incorporated by reference herein in their entireties.

The expression levels of an antibody molecule can be increased by vector amplification. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibodies thus produced, whether polyclonal or monoclonal, can be used, e.g., in an immobilized form bound to a solid support by well known methods.

Antibodies against the antigenic peptides of the invention can also be used, unlabeled or labeled by standard methods, as the basis for immunoassays and immunospecific binding to ARL-1. The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, 1994, Id.).

In particular, the antibodies of the present invention may also be used in conjunction with both fresh-frozen and/or formalin-fixed, paraffin-embedded tissue blocks prepared for study by immunohistochemistry (IHC). For example, immunohistochemistry may be utilized to evaluate tumor tissue for expression of ARL-1 species.

Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions that can be conjugated to antibodies for use as diagnostics according to the present invention. The particular label used will depend upon the type of immunoassay. Examples of labels that can be used include but are not limited to radiolabels such as $^3$H, $^{14}$C, $^{32}$P, $^{125}$I, $^{131}$I, $^{111}$In or $^{99}$Tc; fluorescent labels such as fluorescein and its derivatives, rhodamine and its derivatives, dansyl and umbelliferone; chemiluminescers such as luciferase and 2,3-dihydro-phthalazinediones; and enzymes such as horseradish peroxidase, alkaline phosphatase, lysozyme, glucose-6-phosphate dehydrogenase, and acetylcholinesterase. The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, for example, in IMMUNOASSAY: A PRACTICAL GUIDE (1987, Chan (Ed.), Academic Press, Inc.: Orlando, Fla.).

Further, antibodies of the invention may also be used as therapeutic agents in treating cancer, particularly lung and liver cancer where ARL-1 is overexpressed relative to normal liver and lung tissues. An antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepachlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Alternatively, antibody treatment itself, for example with neutralizing antibodies (deactivating functional ARL-1), can be efficacious if it blocks detoxification or enhances the sensitivity of antitumor agents that are ARL-1 substrates. The high specificity of the antibodies of this invention are advantageous, since this property of the antibodies minimizes cross-reactivity with other members of the AKR superfamily of related proteins, and hence reduces cytotoxicity in normal tissues.

The invention also provides a kit containing an antibody of the invention, preferably conjugated to a detectable substance, and instructions for use. Still another aspect of the invention is a pharmaceutical composition comprising an antibody of the invention. In one embodiment, the pharmaceutical composition comprises an antibody of the invention and a pharmaceutically acceptable carrier.

Also provided are related epitope compounds within the understanding of those with skill in the art, such as chemical mimetics, organomimetics or peptidomimetics. As used herein, the terms "mimetic," "peptide mimetic," "peptidomimetic," "organomimetic" and "chemical mimetic" are intended to encompass peptide derivatives, peptide analogues and chemical compounds having an arrangement of atoms is a three-dimensional orientation that is equivalent to that of a peptide of the invention and form an antigenic epitope sufficient to raise antibodies, including polyclonal antisera and monoclonal antibodies, that are immunologically equivalent to the native peptide epitope. It will be understood that the phrase "immunologically equivalent to" as used herein is intended to encompass compounds having substitution of certain atoms or chemical moieties in said peptide with moieties having bond lengths, bond angles and arrangements thereof in the mimetic compound that produce the same or sufficiently similar arrangement or orientation of said atoms and moieties to be recognized by antibodies having the complementary arrangement of amino acids to produce substantially the same antigen binding site in said antibodies and that bind to the native epitope with substantially the same affinity and avidity. In the peptide mimetics of the invention, the three-dimensional arrangement of the chemical constituents is structurally and/or functionally equivalent to the three-dimensional arrangement of the peptide backbone and component amino acid sidechains in the peptide, resulting in such peptido-, organo- and chemical mimetics of the peptides of the invention having substantial biological activity. These terms are used according to the understanding in the art, as illustrated for example by Fauchere, 1986, Adv. Drug Res. 15: 29; Veber & Freidinger, 1985, TINS p. 392; and Evans et al., 1987, J. Med. Chem. 30: 1229, incorporated herein by reference.

It is understood that the peptide portion of ARL-1 protein used as an antigen for raiding the antibodies of the invention comprises an epitope that defines the chemical and three-dimensional structure of these antibodies. This antigenic epitope is understood in the art as comprising a three-dimensional structure that defines the immunological activity of the epitope. Peptido-, organo- and chemical mimetics can be designed to fit each epitope with current computer modeling software (computer aided drug design). Said mimetics are produced by structure-function analysis, based on the positional information from the substituent atoms in the peptides of the invention.

Peptides as provided by the invention can be advantageously synthesized by any of the chemical synthesis techniques known in the art, particularly solid-phase synthesis techniques, for example, using commercially-available automated peptide synthesizers. Mimetics of the present invention can be synthesized by solid phase or solution phase methods conventionally used for the synthesis of peptides (see, for example, Merrifield, 1963, J. Amer. Chem. Soc. 85: 2149-54; Carpino, 1973, Acc. Chem. Res. 6: 191-98; Birr, 1978, ASPECTS OF THE MERRIFIELD PEPTIDE SYNTHESIS, Springer-Verlag: Heidelberg; THE PEPTIDES: ANALYSIS, SYNTHESIS, BIOLOGY, Vols. 1, 2, 3, 5, (Gross & Meinhofer, eds.), Academic Press: New York, 1979; Stewart et al., 1984, SOLID PHASE PEPTIDE SYNTHESIS, 2nd. ed., Pierce Chem. Co.: Rockford, Ill.; Kent, 1988, Ann. Rev. Biochem. 57: 957-89; and Gregg et al., 1990, Int. J. Peptide Protein Res. 55: 161-214 which are incorporated herein by reference in their entirety.)

The use of solid phase methodology is preferred. Briefly, an N-protected C-terminal amino acid residue is linked to an insoluble support such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization and coupling of successive protected amino acid derivatives are used to link the amino acids from the C-terminus according to the amino acid sequence. For some synthetic peptides, an FMOC strategy using an acid-sensitive resin may be used. Preferred solid supports in this regard are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin (Wang resin), 4-(2',4'-dimethoxyphenylaminomethyl)-phenoxymethyl resin, 2,4-dimethoxybenzhydryl-amine resin, and 4-(2', 4'-dimethoxyphenyl-FMOC-amino-methyl)-phenoxyacetamidonorleucyl-MBHA resin (Rink amide MBHA resin). In addition, acid-sensitive resins also provide C-terminal acids, if desired. A particularly preferred protecting group for alpha amino acids is base-labile 9-fluorenylmethoxy-carbonyl (FMOC).

Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys(Trit), FMOC-Ser (But), FMOC-Asn(Trit), FMOC-Leu, FMOC-Thr(Trit), FMOC-Val, FMOC-Gly, FMOC-Lys(Boc), FMOC-Gln (Trit), FMOC-Glu(OBut), FMOC-His(Trit), FMOC-Tyr (But), FMOC-Arg(PMC (2,2,5,7,8-pentamethylchroman-6- sulfonyl)), FMOC-Arg(BOC)$_2$, FMOC-Pro, and FMOC-Trp (BOC). The amino acid residues can be coupled by using a variety of coupling agents and chemistries known in the art, such as direct coupling with DIC (diisopropyl-carbodiimide), DCC (dicyclohexylcarbodiimide), BOP (benzotriazolyl-N-oxytrisdimethylaminophosphonium hexa-fluorophosphate), PyBOP (benzotriazole-1-yl-oxy-tris-pyrrolidinophosphonium hexafluoro-phosphate), PyBrOP (bromo-tris-pyrrolidinophosphonium hexafluorophosphate); via performed symmetrical anhydrides; via active esters such as pentafluorophenyl esters; or via performed HOBt (1-hydroxybenzotriazole) active esters or by using FMOC-amino acid fluoride and chlorides or by using FMOC-amino acid-N-carboxy anhydrides. Activation with HBTU (2-(1H-benzotriazole-1-yl),1,1,3,3-tetramethyluronium hexafluoro-phosphate) or HATU (2-(1H-7-aza-benzotriazole-1-yl),1,1,3,3-tetramethyluronium hexafluoro-phosphate) in the presence of HOBt or HOAt (7-azahydroxybenztriazole) is preferred.

The solid phase method can be carried out manually, although automated synthesis on a commercially available peptide synthesizer (e.g., Applied Biosystems 431A or the like; Applied Biosystems, Foster City, Calif.) is preferred. In a typical synthesis, the first (C-terminal) amino acid is loaded on the chlorotrityl resin. Successive deprotection (with 20% piperidine/NMP (N-methylpyrrolidone)) and coupling cycles according to ABI FastMoc protocols (ABI user bulletins 32 and 33, Applied Biosystems) are used to build the whole peptide sequence. Double and triple coupling, with capping by acetic anhydride, may also be used.

The synthetic peptides, or when appropriate synthetic mimetic peptides, are cleaved from the resin and deprotected by treatment, for example, with TFA (trifluoroacetic acid) containing appropriate scavengers. Many such cleavage reagents, such as Reagent K (0.75 g crystalline phenol, 0.25 mL ethanedithiol, 0.5 mL thioanisole, 0.5 mL deionized water, 10 mL TFA) and others, can be used. The peptide is separated from the resin by filtration and isolated by ether precipitation. Further purification may be achieved by conventional methods, such as gel filtration and reverse phase HPLC (high performance liquid chromatography). Synthetic mimetics according to the present invention may be in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization out of the appropriate base.

Generally, those skilled in the art will recognize that peptides as described herein may be modified by a variety of chemical techniques to produce compounds forming essentially the same immunological epitope as the unmodified peptide, and optionally having other desirable properties. For example, carboxylic acid groups of the peptide may be provided in the form of a salt of a pharmaceutically-acceptable cation. Amino groups within the peptide may be in the form of a pharmaceutically-acceptable acid addition salt, such as the HCl, HBr, acetic, benzoic, toluene sulfonic, maleic, tartaric and other organic salts, or may be converted to an amide. Thiols can be protected with any one of a number of well-recognized protecting groups, such as acetamide groups. Those skilled in the art will also recognize methods for introducing cyclic structures into the peptides of this invention so that the native binding configuration will be more nearly approximated. For example, a carboxyl terminal or amino terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Specifically, a variety of techniques are available for constructing peptide derivatives and analogues with the same or similar desired immunological activity as the corresponding peptide compound but with more favorable activity than the peptide with respect to solubility, stability, and susceptibility to hydrolysis and proteolysis. Such derivatives and analogues include peptides modified at the N-terminal amino group, the C-terminal carboxyl group, and/or changing one or more of the amido linkages in the peptide to a non-amido linkage. It will be understood that two or more such modifications can be coupled in one peptide mimetic structure (e.g., modification at the C-terminal carboxyl group and inclusion of a —CH$_2$—carbamate linkage between two amino acids in the peptide).

Amino terminus modifications include alkylating, acetylating, adding a carbobenzoyl group, and forming a succinimide group. Specifically, the N-terminal amino group can then be reacted to form an amide group of the formula RC(O)NH— where R is alkyl, preferably lower alkyl, and is added by reaction with an acid halide, RC(O)Cl or acid anhydride. Typically, the reaction can be conducted by contacting about equimolar or excess amounts (e.g., about 5 equivalents) of an acid halide to the peptide in an inert diluent (e.g., dichloromethane) preferably containing an excess (e.g., about 10 equivalents) of a tertiary amine, such as diisopropylethylamine, to scavenge the acid generated during reaction. Reaction conditions are otherwise conventional (e.g., room temperature for 30 minutes). Alkylation of the terminal amino to provide for a lower alkyl N-substitution followed by reaction with an acid halide as described above will provide for N-alkyl amide group of the formula RC(O)NR—. Alternatively, the amino terminus can be covalently linked to succinimide group by reaction with succinic anhydride. An approximately equimolar amount or an excess of succinic anhydride (e.g., about 5 equivalents) are used and the terminal amino group is converted to the succinimide by methods well known in the art including the use of an excess (e.g., ten equivalents) of a tertiary amine such as diisopropylethylamine in a suitable inert solvent (e.g., dichloromethane), as described in Wollenberg et al., U.S. Pat. No. 4,612,132, is incorporated herein by reference in its entirety. It will also be understood that the succinic group can be substituted with, for example, $C_2$- through $C_6$-alkyl or —SR substituents, which are prepared in a conventional manner to provide for substituted succinimide at the N-terminus of the peptide. Such alkyl substituents are prepared by reaction of a lower olefin ($C_2$- through $C_6$-alkyl) with maleic anhydride in the manner described by Wollenberg et al., supra., and —SR substituents are prepared by reaction of RSH with maleic anhydride where R is as defined above. In another advantageous embodiments, the amino terminus is derivatized to form a benzyloxycarbonyl-NH— or a substituted benzyloxycarbonyl-NH— group. This derivative is produced by reaction with approximately an equivalent amount or an excess of benzyloxycarbonyl chloride (CBZ-Cl) or a substituted CBZ-Cl in a suitable inert diluent (e.g., dichloromethane) preferably containing a tertiary amine to scavenge the acid generated during the reaction. In yet another derivative, the N-terminus comprises a sulfonamide group by reaction with an equivalent amount or an excess (e.g., 5 equivalents) of R—S(O)$_2$Cl in a suitable inert diluent (dichloromethane) to convert the terminal amine into a sulfonamide, where R is alkyl and preferably lower alkyl. Preferably, the inert diluent contains excess tertiary amine (e.g., ten equivalents) such as diisopropylethylamine, to scavenge the acid generated during reaction. Reaction conditions are otherwise conventional (e.g., room temperature for 30 minutes). Carbamate groups are produced at the amino terminus by reaction with an equivalent amount or an excess (e.g., 5 equivalents) of R—OC(O)Cl or R—OC(O)OC$_6$H$_4$-p-NO$_2$ in a suitable inert diluent (e.g., dichloromethane) to convert the terminal amine into a carbamate, where R is alkyl, preferably lower alkyl. Preferably, the inert diluent contains an excess (e.g., about 10 equivalents) of a tertiary amine, such as diisopropylethylamine, to scavenge any acid generated during reaction. Reaction conditions are otherwise conventional (e.g., room temperature for 30 minutes). Urea groups are formed at the amino terminus by reaction with an equivalent amount or an excess (e.g., 5 equivalents) of R—N=C=O in a suitable inert diluent (e.g., dichloromethane) to convert the terminal amine into a urea (i.e., RNHC(O)NH—) group where R is as defined above. preferably, the inert diluent contains an excess (e.g., about 10 equivalents) of a tertiary amine, such as diisopropylethylamine. Reaction conditions are otherwise conventional (e.g., room temperature for about 30 minutes).

In preparing peptide mimetics wherein the C-terminal carboxyl group is replaced by an ester (e.g., —C(O)OR where R is alkyl and preferably lower alkyl), resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester. In preparing peptide mimetics wherein the C-terminal carboxyl group is replaced by the amide —C(O)NR$_3$R$_4$, a benzhydrylamine resin is used as the solid support for peptide synthesis. Upon completion of the synthesis, hydrogen fluoride treatment to release the peptide from the support results directly in the free peptide amide (i.e., the C-terminus is —C(O)NH$_2$). Alternatively, use of the chloromethylated resin during peptide synthesis coupled with reaction with ammonia to cleave the side chain Protected peptide from the support yields the free peptide amide and reaction with an alkylamine or a dialkylamine yields a side chain protected alkylamide or dialkylamide (i.e., the C-terminus is —C(O)NRR$_1$, where R and R$_1$ are alkyl and preferably lower alkyl). Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by displacement of the —OH or the ester (—OR) of the carboxyl group or ester respectively with the N-terminal amino group to form a cyclic peptide. For example, after synthesis and cleavage to give the peptide acid, the free acid is converted in solution to an activated ester by an appropriate carboxyl group activator such as dicyclohexylcarbodiimide (DCC), for example, in methylene chloride (CH$_2$Cl$_2$), dimethyl formamide (DMF), or mixtures thereof. The cyclic peptide is then formed by displacement of the activated ester with the N-terminal amine. Cyclization, rather than polymerization, can be enhanced by use of very dilute solutions according to methods well known in the art.

Peptide mimetics as understood in the art and provided by the invention are structurally similar to the paradigm peptide of the invention, but have one or more peptide linkages optionally replaced by a linkage selected from the group consisting of: —CH$_2$NH—, —CH$_2$S—, —CH$_2$CH$_2$—, —CH=CH— (in both cis and trans conformers), —COCH$_2$—, —CH(OH)CH$_2$—, and —CH$_2$SO—, by methods known in the art and further described in the following references: Spatola, 1983, in CHEMISTRY AND BIOCHEMISTRY OF AMINO ACIDS, PEPTIDES, AND PROTEINS, (Weinstein, ed.), Marcel Dekker: New York, p. 267; Spatola, 1983, *Peptide Backbone Modifications* 1: 3; Morley, 1980, *Trends Pharm. Sci.* pp. 463-468; Hudson et al., 1979, *Int. J. Pept. Prot. Res.* 14: 177-185; Spatola et al., 1986, *Life Sci.* 38: 1243-1249; Hann, 1982, *J. Chem. Soc. Perkin Trans*. I 307-314; Almquist et al., 1980, *J. Med. Chem.* 23: 1392-1398; Jennings-White et al., 1982, *Tetrahedron Lett.* 23: 2533; Szelke et al., 1982, European Patent Application, Publication No. EP045665A; Holladay et al., 1983, *Tetrahedron Lett.* 24: 4401-4404; and Hruby, 1982, *Life Sci.* 31: 189-199, each of which is incorporated herein by reference. Such peptide mimetics may have significant advantages over polypeptide embodiments, including, for example: being more economical to produce, having greater chemical stability or enhanced pharmacological properties (such half-life, absorption, potency, efficacy, etc.), enhanced antigenicity, and other properties.

Mimetic analogs of the epitope peptides of the invention may also be obtained using the principles of conventional or rational drug design (see, Andrews et al., 1990, *Proc. Alfred Benzon Symp.* 28: 145-165; McPherson, 1990, *Eur. J. Biochem.* 189:1-24; Hol et al., 1989a, in MOLECULAR RECOGNITION: CHEMICAL AND BIOCHEMICAL PROBLEMS, (Roberts, ed.); Royal Society of Chemistry; pp. 84-93; Hol, 1989b, *Arzneim-Forsch.* 39:1016-1018; Hol, 1986, *Agnew Chem. Int. Ed. Engl.* 25: 767-778, the disclosures of which are herein incorporated by reference).

In accordance with the methods of conventional drug design, the desired mimetic molecules are obtained by randomly testing molecules whose structures have an attribute in common with the structure of a "native" peptide. The quantitative contribution that results from a change in a particular group of a binding molecule can be determined by measuring the biological activity of the putative mimetic in comparison with the antigenic capacity, or binding affinity to the antibodies of the invention, of the native peptide. In a preferred embodiment of rational drug design, the mimetic is designed to share an attribute of the most stable three-dimensional conformation of the peptide. Thus, for example, the mimetic may be designed to possess chemical groups that are oriented in a way sufficient to cause ionic, hydrophobic, or van der Waals interactions that are similar to those exhibited by the antigenic capacity, or binding affinity to the antibodies of the invention, of the native peptides of the invention, as disclosed herein.

The preferred method for performing rational mimetic design employs a computer system capable of forming a representation of the three-dimensional structure of the peptide, such as those exemplified by Hol, 1989a, ibid.; Hol, 1989b, ibid.; and Hol, 1986, ibid. Molecular structures of the peptido-, organo- and chemical mimetics of the peptides of the invention are produced according to those with skill in the art using computer-assisted design programs commercially available in the art. Examples of such programs include SYBYL 6.5®, HQSAR™, and ALCHEMY 2000™ (Tripos); GALAXY™ and AM2000™ (AM Technologies, Inc., San Antonio, Tex.); CATALYST™ and CERIUS™ (Molecular Simulations, Inc., San Diego, Calif.); CACHE PRODUCTS™, TSAR™, AMBER™, and CHEM-X™ (Oxford Molecular Products, Oxford, Calif.) and CHEMBUILDER3D™ (Interactive Simulations, Inc., San Diego, Calif.).

The peptido-, organo- and chemical mimetics produced using the peptides disclosed herein using, for example, art-recognized molecular modeling programs are produced using conventional chemical synthetic techniques, most preferably designed to accommodate high throughput screening, including combinatorial chemistry methods. Combinatorial methods useful in the production of the peptido-, organo- and chemical mimetics of the invention include phage display arrays, solid-phase synthesis and combinatorial chemistry arrays, as provided, for example, by SIDDCO, Tuscon, Ariz.; Tripos, Inc.; Calbiochem/Novabiochem, San Diego, Calif.; Symyx Technologies, Inc., Santa Clara, Calif.; Medichem Research, Inc., Lemont, Ill.; Pharm-Eco Laboratories, Inc., Bethlehem, Pa.; or N.V. Organon, Oss, Netherlands. Combinatorial chemistry production of the peptido-, organo- and chemical mimetics of the invention are produced according to methods known in the art, including but not limited to techniques disclosed in Terrett, 1998, COMBINATORIAL CHEMISTRY, Oxford University Press, London; Gallop et al., 1994, "Applications of combinatorial technologies to drug discovery. 1. Background and peptide combinatorial libraries," *J. Med. Chem.* 37: 1233-51; Gordon et al., 1994, "Applications of combinatorial technologies to drug discovery. 2. Combinatorial organic synthesis, library screening strategies, and future directions," *J. Med. Chem.* 37: 1385-1401; Look et al., 1996, *Bioorg. Med. Chem. Lett.* 6: 707-12; Ruhland et al., 1996, *J. Amer. Chem. Soc.* 118: 253-4; Gordon et al., 1996, *Acc. Chem. Res.* 29: 144-54; Thompson & Ellman, 1996, *Chem. Rev.* 96: 555-600; Fruchtel & Jung, 1996, *Angew. Chem. Int. Ed. Engl.* 35: 17-42; Pavia, 1995, "The Chemical Generation of Molecular Diversity," Network Science Center, www-.netsci.org; Adnan et al., 1995, "Solid Support Combinatorial Chemistry in Lead Discovery and SAR Optimization," Id., Davies and Briant, 1995, "Combinatorial Chemistry Library Design using Pharmacophore Diversity," Id., Pavia, 1996, "Chemically Generated Screening Libraries: Present and Future," Id.; and U.S. Pat. Nos. 5,880,972 to Horlbeck; 5,463,564 to Agrafiotis et al.; 5,331,573 to Balaji et al.; and 5,573,905 to Lerner et al.

Kits as provided by the invention comprise antibodies of the invention, in embodiments that are polyclonal antisera, monoclonal antibodies or fragments or derivatives thereof, and instructions for their use. The components of the kit are advantageously provided in a container to preserve their integrity. In certain embodiments, the antibodies of the invention are provided in dry form, as powders or lyophilizates, and in these embodiments the kit advantageously includes liquid buffers or other reagents for reconstitution of the dry antibody preparations, as well as instructions for such reconstitution. Certain embodiments of the kits of the invention include reagents, in dried or liquid form, for use in the practice of the methods of the invention. These reagents can include, inter alia, buffers, salts, hybridization solutions, washing solutions, secondary antibodies, reagents for labeling primary or secondary antibodies, and reagents such as enzyme substrates for developing the results of, for example, an in situ hybridization assay. Instructions for use of any of these reagents are also advantageously included in such kits.

ARL-1 protein is over expressed in human breast carcinoma, human hepatocellular carcinoma and lung squamous cell carcinoma and adenocarcinoma. ARL-1 protein is underexpressed or expression is lost in gastrointestinal cancer and precancerous lesions. Thus, ARL-1 is a marker for the diagnosis and/or early diagnosis of cancer, using the antibodies of the invention. In the use of the antibodies of the invention overexpression of ARL-1 is detected for the diagnosis and early diagnosis of certain tumors, such as breast carcinoma, hepatocellular carcinoma and lung cancer, and underexpression or loss of expression of ARL-1 is detected in other tumor types, including gastrointestinal carcinoma and specifically small and large bowel cancers. Any immunologically-based assay can be used for these diagnostic embodiments, including immunohistochemistry of tissue samples, radioimmune assay or ELISA assay of bodily fluids or exudates, FACS analysis of shed epithelial cells in stool, and other methods and tumor sample sources known to those with skill in the art. Also, a determination that a precancerous or biopsy specimen shows reduction or loss of ARL-1 expression, even in the absence of clinical manifestations of disease, is a risk factor for development of cancer in gastrointestinal organs and tissues. ARL-1 related detection in body fluids include the detection of ARL-1 protein and ARL-1 antibodies that may be produced in humans in responding to ARL-1 protein in normal or cancer cells.

The description set forth above and the Examples set forth below recite exemplary embodiments of the invention. However, the disclosure set forth herein is intended to encompass any biologic anticancer agent useful against any tumor cell type for which resistance can be developed. The following Examples are intended to further illustrate certain preferred embodiments of the invention and are not limiting in nature.

EXAMPLES

Example 1

Preparation of Antigenic Peptide by Solid Phase Peptide Synthesis

A peptide (having the amino acid sequence: DDKGNAIG-GKATFLC; SEQ ID NO. 1) provided by the invention for use as specific antigen for raising the anti-ARL-1 antibodies of the invention was prepared as follows.

Solid phase peptide synthesis (SPPS) was carried out on a 0.25 millimole (mmole) scale using an Applied Biosystems Model 431A Peptide Synthesizer and using 9-fluorenylmethyl-oxycarbonyl (Fmoc) amino-terminus protection, coupling with dicyclohexylcarbodiimide/hydroxybenzotriazole or 2-(1H-benzotriazol-1-yl)-1,1,3,3-tetramethyluronium hexafluoro-phosphate/hydroxybenzotriazole (HBTU/HOBT), and using p-hydroxymethyl phenoxymethyl-polystyrene (HMP) resin or Sasrin™, or chlorotrityl resin for carboxyl-terminus acids or Rink amide resin for carboxyl-terminus amides.

Sasrin™ resin-bound peptides are cleaved using a solution of 1% TFA in dichloromethane to yield the protected peptide. Where appropriate, protected peptide precursors are cyclized between the amino- and carboxyl-termini by reaction of sidechain-protected, amino-terminal free amine and car-boxyl-terminal free acid using diphenylphosphorylazide.

HMP or Rink amide resin-bound products are routinely cleaved and protected cyclized peptides deprotected using a solution comprised of trifluoroacetic acid (TFA), or TFA and methylene chloride, optionally comprising water, thioanisole, ethanedithiol, and triethylsilane or triisopropylsilane in ratios of 100:5:5:2.5:2, for 0.5-3 hours at room temperature. Where appropriate, products were re-S-tritylated in triphenolmethanol/TFA, and N-Boc groups re-introduced into the peptide using $(Boc)_2O$.

Crude peptides are purified by preparative high pressure liquid chromatography (HPLC) using a Waters Delta Pak C18 column and gradient elution using 0.1% trifluoroacetic acid (TFA) in water modified with acetonitrile. Acetonitrile is evaporated from the eluted fractions which are then lyophilized. The identity of each product is confirmed by fast atom bombardment mass spectroscopy (FABMS) or by electrospray mass spectroscopy (ESMS).

Example 2

Preparation of Polyclonal Antibodies

Polyclonal antibodies specific for the ARL-1 protein species were prepared using the epitopic peptide disclosed in Example 1. Polyclonal antibodies against an oligopeptide of SEQ ID NO. 1 prepared according to Example 1, or against purified recombinant peptide of SEQ ID NO. 1, were generated in rabbits according to standard procedures well known in the art (see, for example, Harlow & Lane, Id.). Briefly, purified peptides were conjugated with keyhole limpet hemocyanin (KLH) using conventional methods (Harlow & Lane, Id.) and immunization were performed below:

| Day | 0 | Pre-immunization bleed | |
|---|---|---|---|
| Day | 0 | Initial immunization (KLH) | 500 ug (CFA) |
| Day | 14 | Boost (KLH) | 250 ug (IFA) |
| Day | 28 | Boost (KLH) | 250 ug (IFA) |
| Day | 37 | Test bleed (~5 ml) | ~5.0 ml |
| Day | 42 | Boost (KLH) | 250 ug (IFA) |
| Day | 59 | Terminal bleed (Exsanguination) | (~70 – 100 ml) |

The polyclonal antisera obtained from these animals were used in Western blots performed using conventional methods and protocols. Briefly stated, cells expressing different AKR superfamily members were lysed on ice for 30 min with lysis buffer (containing 10 mM HEPES, 10 mM KCl, 1 mM EDTA (pH 8.0), 0.1% NP-40, 1 mM DTT, 1 mM PMSF and 0.5 mM $Na_3VO_4$). Soluble protein (30 µg) or purified AR and ARL-1 protein (2 µg) was separated on a 12% SDS-PAGE gel and blotted onto a pure nitrocellulose membrane (Bio-Rad, CA) at 180 mA for 2 hours. After blockage with 5% skim milk in PBS at room temperature for 45 min, membranes were incubated with ARL-1 antibody-containing polyclonal antisera (1:500) in the same buffer for 1 hour or at 4° C. overnight, followed by incubation with goat anti-rabbit IgG (1:2000) for 1 hour. Antibody binding was detected using an enhanced chemiluminescence system (Pierce, Ill.). To correct protein loading amounts, membranes were re-probed with β-actin monoclonal antibody (1:40,000).

The specificity of the polyclonal antisera disclosed herein is shown in FIG. 1A, which is a photograph of Western blot analyses of three antisera used as probes of blotted recombinant ARL protein species. The results shown in FIG. 1 demonstrated that the ARL-1 antisera of this invention were the only antisera showing specificity for ARL-1 species shown herein to be differentially expressed in gastrointestinal tissues. Both of the other antisera testes showed varying levels of cross-reactivity with other AKR species, including extensive cross-reactivity with ARL-1A1, -1B1 and -1C2. These results established that the ARL-1-reactive antisera of this invention are specific for the ARL-1 species differentially expressed in gastrointestinal tissues including stomach, small intestine and colon.

Specificity of the antibodies of the invention was further shown by the experimental results set forth in FIGS. 1B and 1C. Whole cell lysates from human A549 cells (which express both ARL-1 and related AR proteins) in increasing cell numbers (Lane 2: 10,000 cells; Lane 3: 50,000 cells; Lane 4: 100,000 cells) were mixed with an equal volume of 2×SDS loading buffer and heated to 75° C. for 10 min. Before being loaded on an SDS-polyacrylamide gel and subjected to electrophoresis. The gel was then stained with Coomassie blue stain (left panel) and subjected to Western blot analysis as described above. AR (middle panel) and ARL-1 (AKR1B10; right panel) proteins were detected.

FIG. 1C shows results obtained using both cell lysates and purified protein subjected to SDS-PAGE and Western blot analysis as set forth above. Western blots were probed with antibodies specific for AR (middle panel) or ARL-1 (AKR1B10; right panel) and showed AR cross-reactivity against purified AR protein (Lane 1) and 293T cell lysates (that express AR but not ARL-1 protein; Lane 3), as well as ARL-1 cross-reactivity to ARL-1 purified protein (Lane 2) and HCT-8 cell lysates (that express ARL-1 but not AR protein; Lane 4).

Example 3

Analysis of ARL-1 Expression in Normal, Precancerous and Cancer Tissues of the GI Tract The ARL-1 specific polyclonal antisera prepared as set forth in Example 2 was used to investigate expression of ARL-1 protein in normal human gastrointestinal tract, precancerous lesions and cancers. Previously the inventor had shown that this protein was overexpressed in hepatocarcinoma (Cao et al., 1998, Id.) and overexpression of ARL-1 was independently demonstrated in certain lung cancers (Fukumoto et al., 2005, *Clin Cancer Res.* 11:1776-85.). However, little was known about ARL-1 expression in stomach, small intestine and colon prior to this invention.

Expression in human colon epithelia was demonstrated using immunohistochemical methods as set forth in Martinet et al. (2006, *Autophagy* 2: 55-57). Briefly, formalin-fixed paraffin-embedded sections were dewaxed and stained with polyclonal antisera of the invention at a dilution of 1:5. Hematoxylin counter staining was used to indicate nuclei. The results of these assays are shown in FIG. 2. Results indicated that ARL-1 protein was specifically expressed at very high level in epithelial cells of the colon. To understand the maturation of the ARL-1 expression cells, adjacent sections were stained with Ki-67, a marker of proliferating cells, and the results clearly indicated that ARL-1 and Ki-67 were expressed in distinct cell populations. ARL-1 cells were shown by these experiments to be expressed in terminally-differentiated colon epithelia. Equivalent results were obtained when section of normal stomach and small intestine were assayed as described herein (data not shown).

Figure 4:
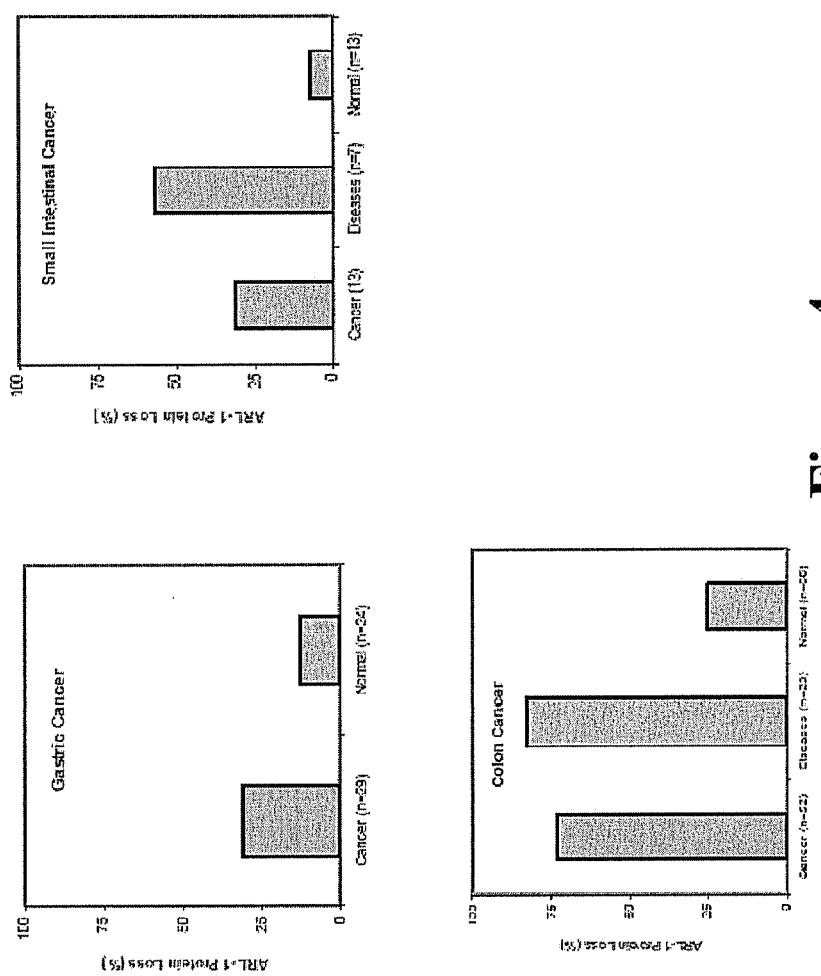
FIG. 4 is a graphical representation of ARL-1 protein loss in gastric, colon, and small bowel tissues. ARL-1 protein levels were examined by Western blot, as indicated in FIG. 3. Results are indicated as the percentage of ARL-1 loss samples over the total tested specimens. Normal indicates the matching normal tissues, and disease denotes precancerous disease samples.

To investigate the role of ARL-1 in colon tumorigenesis, mRNA and protein expression of ARL-1 gene in gastrointestinal (GI) cancer tissues was investigated. After electrophoretic separation of 50 µg solubilized protein per sample, Western blot analysis was performed as described in Example 2. ARL-1 polyclonal antisera prepared as set forth in Example 2 was used at a dilution of 1:500. Protein loading amounts per well were corrected by probing with β-actin monoclonal antibody (Sigma, St. Louis, Mo.). The results of these assays are shown in FIG. 3, where colon cancer sample were paired with normal surrounding tissues. As seen in the Figure, ARL-1 protein was undetectable in Tumor 2, 4, and 5, and was dramatically decreased in Tumor 3, compared to the paired normal tissue. Western blot assays were performed on a total of 29 gastric, 13 small bowel, and 52 colon cancer tissues, the majority of which were paired with surrounding normal tissues. ARL-1 protein levels were also checked in the surgical specimens of small intestinal (n=7) and colon (n=23) precancerous diseases. FIG. 4 shows the results obtained in these assays, indicating that in many GI disease and cancer tissues, especially in the colon, ARL-1 protein was undetectable. Interestingly, ARL-1 protein was also undetectable in some matched normal tissues, indicating genetic loss of ARL-1 protein in these patients (FIG. 4). These results are significant, because they suggest that ARL-1 loss may be a risk factor of GI cancer by leaving the GI cells vulnerable to dietary carbonyl carcinogens. Thus, ARL-1 can serve as marker useful for identifying individuals at risk for developing gastrointestinal cancer due to the loss of this protein protection against carcinogenic reactive carbonyls, particularly dietary carbonyls. These results also suggest that ARL-1 is a candidate for developing specific intervention agents that target to ARL-1, which will significantly prevent GI cancer.

Figure 5:
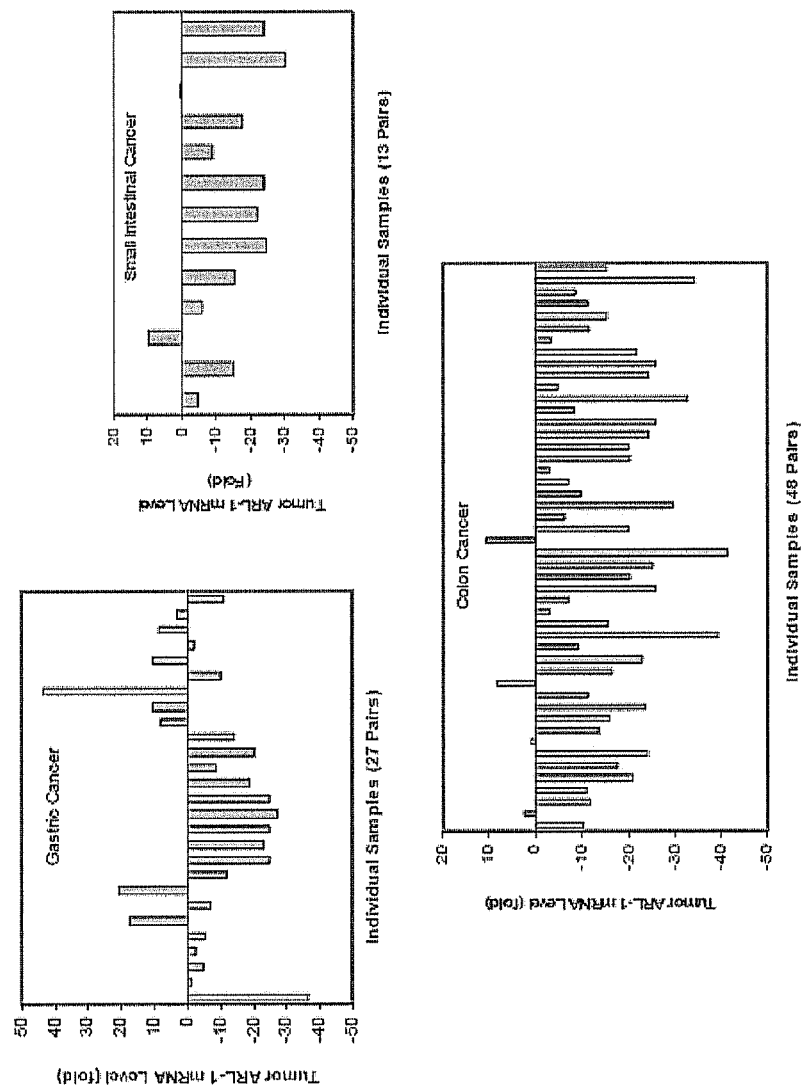
FIG. 5 is a graphical representation of the results of quantitative analysis of ARL-1 mRNA in gastric, colon, and small bowel tissues using real-time PCR. The results were expressed as fold of ARL-1 mRNA levels in tumor over in the matching normal tissue. Negative indicates decrease of mRNA in tumor tissues while positive indicates increase. In this study, only the tumor tissues with matching normal tissues were investigated.

ARL-1 gene expression was investigated using quantitative real-time PCR to determine mRNA levels of this gene in normal and colon cancer tissues. Real-time PCR was performed using ARL-1 specific primers according to the manufacturer's instructions (Applied Biosystems, CA). The primer and probes are commercially purchased from Applied Biosystems (Catalog number: Hs00252524_m1, Foster City, Calif.). In this study, only tumor samples with matching normal tissues were examined for the comparison purpose. The results are shown in FIG. 5 as the "fold" changes in ARL-1 mRNA levels. In this Figure, negative results reveal decrease of ARL-1 mRNA levels in colon cancer samples.

These results established that ARL-1 expression was reduced in a significant proportion of human gastrointestinal tumors and precancerous lesions, a result consistent with ARL-1's purported role in providing these tissues with protection from reactive carbonyl species.

Figure 6:
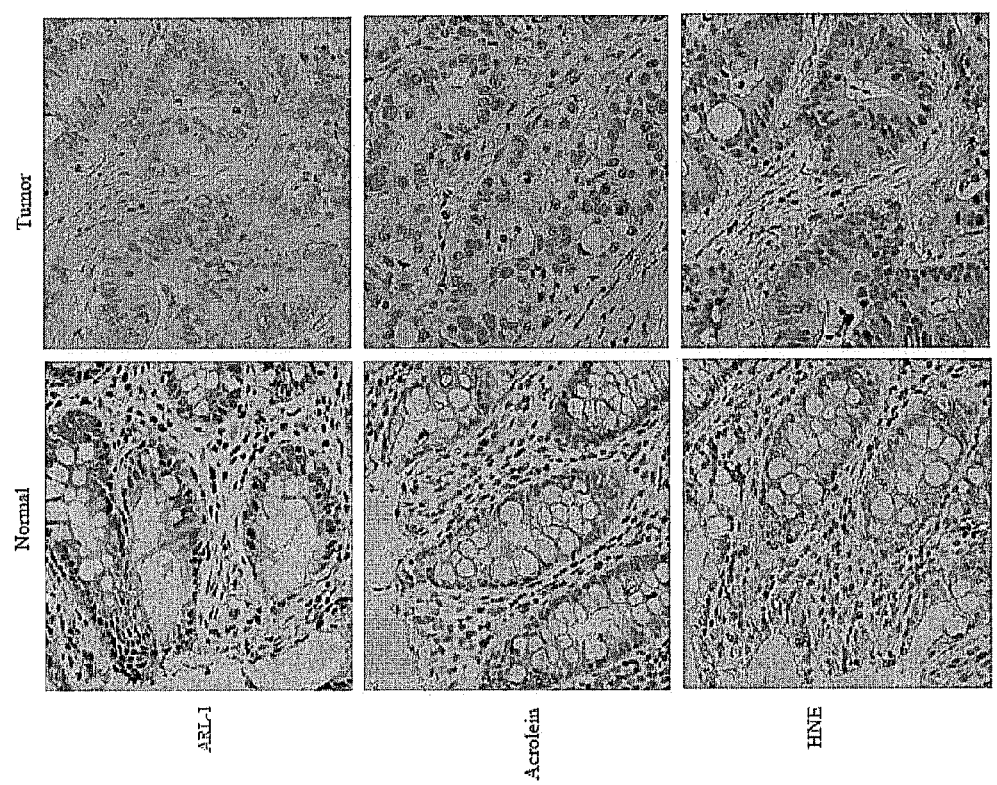
FIG. 6 is a photomicrograph of immunohistochemical analysis of ARL-1 expression and reactive carbonyl adduct formation in normal and colon tumor tissues. Both normal and tumor tissues were from the same cancer patient. Paraffin-embedded sections were used for immunohistochemistry study and assayed for ARL-1 expression and acrolein or 4-hydroxynonenal (HNE) adduct formation. Results indicated ARL-1 significantly prevents the formation of acrolein and HNE adducts. (20× objectives).

The existence of reactive carbonyl-protein adducts in normal and colon tumor tissues was assayed by immunohistochemistry. A role in cytoprotection for ARL-1 suggests that normal colon epithelium displaying ARL-1 activity would show the presence of little or no adducts formed between reactive carbonyls and cellular components (proteins and nucleic acids) compared with colon tumors, which would be expected to show adduct formation to a greater extent due to the loss of ARL-1. Immunohistochemical study of carbonyl adducts is an art-recognized method for detecting carbonyl-protein adducts (Suzuki et al., 1999, *J Am Soc Nephrol* 10:822-832). Accordingly, paired normal and colon tumor tissues were assayed using antibodies (obtained from Chemicon International, CA) against acrolein and 4-hydroxynonenal (HNE) adducts, respectively. These results are shown in FIG. 6, where acrolein and HNE adducts are detected in tumor tissues with reduced ARL-1 expression and not in normal colon epithelia. In paired normal and tumor tissue samples, ARL-1 was expressed in the epithelial cells of normal colon, which efficiently blocked the formations of acrolein and HNE adducts in these cells (arrows). However, in tumor tissue ARL-1 protein was undetectable in cancer cells, and consequently, acrolein and HNE adducts were formed at very high levels in the cells (arrows).

These results indicate that ARL-1 expression is associated with protection of normal colon epithelium from reactive carbonyl adduct formation, a protection lost in colon tumor cells.

Example 4

Analysis of ARL-1 Activity on Dietary-Associated Reactive Carbonyls and its Cellular Protection Enzymatic activity of ARL-1 toward reactive carbonyls were first measured using purified ARL-1 protein, by assaying oxidation of NADPH to NADP$^+$ as described in Cao et al. (1998, Id.). Michaelis-Menten constants ($K_m$ and $V_{max}$) were calculated with GraphPad Prism 4 (Graph Pad Software, CA). These results showed that ARL-1 has strong enzymatic activity to reactive carbonyls.

The capacity for ARL-1 to provide protection to gastrointestinal cells, and the consequences stemming from loss of such capacity, were assessed using an in vitro model system. Human HCT-8 cells, a colon cancer cell line, were purchased from the American Type Culture Collection (ATCC, Manassas, Va.) and grown and maintained in RPM1-1640 medium (Hyclone, Utah), supplemented with 10% fetal bovine serum (FBS), 2 mM glutamine, and 100 U/ml penicillin and 100 µg/mL streptomycin at 37° C., 5% $CO_2$.

To test for intracellular ARL-1 function, two small interfering RNAs (siRNAs) were designed and used to downregulate ARL-1 levels in cultured HCT-8 cells derived from human colon carcinoma. These siRNAs were targeted to encoding region (siRNA 1, 5' GCAAGUUGUGGCCCACU-UUtt; SEQ ID NO: 2) and 3' untranslational region (siRNA 2, 5' CGAGAAUCGAGGUGCUGUUtt; SEQ ID NO: 3), respectively, and were chemically synthesized (obtained from Ambion, Tex.). A randomly-scrambled siRNA was used as a negative control. For siRNA delivery, HCT-8 cells (3.5× $10^3$ to $10^5$ in Opti-MEM I medium) were mixed gently with siRNA and OligofectAMINE (Invitrogen, CA) in a total volume of 0.5~1.5 mL and then incubated at 37° C., 5% $CO_2$ for 4 hours, followed by an addition of equal volumes of fresh medium containing 20% FBS. Cells were allowed to incubate until harvest.

Figures 7A, 7B, 7C, 7D:
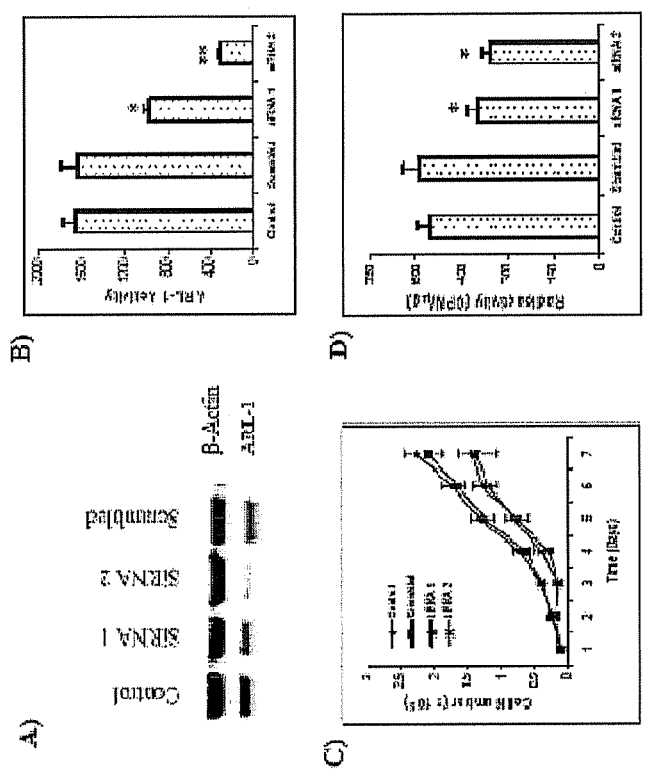
FIGS. 7A through 7D show the effects of ARL-1 knockdown on cell growth. An HCT-8 cell suspension ($3 \times 10^5$) was mixed with siRNA (50 nM) and OligofectAMINE transfection reagent, and then spread into 24-well plates at $10^4$ cells/well for cell growth tests (FIG. 7C). The remaining cells were cultured in 6-well plates for Western blot analysis (FIG. 7A), enzymatic activity (nmoles/mg protein/hour.

The effects of siRNA inhibition of ARL-1 expression was assessed by Western blot analysis (results shown in FIG. 7A), ARL-1 activity (FIG. 7B), cell growth (FIG. 7C) and tritiated thymidine incorporation (FIG. 7D). Western blot analysis was performed as set forth above using the polyclonal antisera of this invention. These results correlated with a decrease in ARL-1 activity in these cells, as shown in FIG. 7B. These assays were performed by assaying oxidation of NADPH to NADP$^+$ as described in Cao et al. (1998, Id.). These results in FIGS. 7A and 7B showed a siRNA-specific decrease in ARL-1 protein and enzymatic activity, consistent with the other results shown herein. These results showed that both siRNA 1 and 2 (50 nM) specifically downregulated ARL-1 protein up to 60 and 95%, respectively.

Having successful reduced ARL-1 expression in these cells provided a cell model system for investigating the intracellular role of this protein in regulating carbonyl stress. Cell growth and DNA synthesis were assayed in cells having reduced ARL-1 expression caused by siRNAs. In cell growth experiments, $10^4$ cells per well were seeded into 24-well plates and incubated at 37° C., 5% $CO_2$ atmosphere and viable cells were counted by trypan blue exclusion staining. These results are shown in FIG. 7C. ARL-1 knockdown significantly inhibited HCT-8 cell growth rate by more than 30% compared to the control cells.

Tritiated thymidine incorporation was assayed as follows. Cells were pulsed with 10 µCi $^3$H-thymidine for 2 hours and then lysed in 15% trichloroacetic acid (TCA) on ice. After washing twice with 15% TCA, acidic-insoluble materials were completely dissolved in 0.1 N NaOH. An aliquot (10 µL) was used to determine protein amount and the remaining was subjected to radioactivity assay. $^3$H-thymidine incorporation was corrected by protein amount as described in Dake et al. (2004, *Endocrinology* 145: 3369-3374). These results are shown in FIG. 7D, where siRNA treated HCT-8 cells incorporated about 30% less tritium into cellular DNA than control cells.

Cytotoxicity comparisons were performed by exposing cells (with ARL-1 knockdown) to acrolein (25 µM) or crotonaldehyde (50 µM) for 72 hours. In these experiments, after the cells were incubated with carbonyl compounds the culture medium was gently removed, and cells were washed with cold PBS and trypsinized. Viable cells were counted by trypan blue exclusion staining.

The mechanisms of cell death induced by reactive carbonyls were investigated by flow cytometry and lactate dehydrogenase leakage assay. For flow cytometry assay, cells (with ARL-1 knockdown) were incubated with acrolein (25 µM) for 24 hours. After medium was gently removed, cells were washed with cold PBS and trypsinized. Cells in PBS and trypsin digestion were pooled, washed with PBS twice at 1200 rpm for 10 min, and then subjected to immediate propidium iodide (PI) and annexin V-FITC staining for 10 minutes in the dark as set forth in Yuan et al. (2004, *Oncogene* 23: 5843-5852, 2004). FACScan analysis was performed using a FACScan cytometer (Becton Dickinson, CA).

For lactate dehydrogenase (LDH) efflux assays, cells were plated at $5 \times 10^4$ cells/well in 12-well plates and exposed to 25 µM of acrolein for 12 hours. Medium was collected and cells were lysed for 10 min in 0.5% (v/v) Triton X-100 in 0.1 M potassium phosphate buffer (pH 7.4). Supernatants were collected by centrifugation at 10,000×g for 5 min. LDH activity in medium and cell lysates was measured using LDH assay kit (Roche, Ind.). Samples (100 µl each, diluted if necessary) were mixed with equal volumes of LDH reagent in 96-well plates. Three wells were prepared for each sample to obtain averages. After incubation at room temperature in the dark for 10 min, reactions were stopped by addition of 50 µl of 1 N HCl. Absorbance at 490 nm was read in a microplate reader (Bio-Rad, CA), with 650 nm as a reference wavelength. LDH release was calculated as: LDH release (%)=[LDH in medium/(LDH in medium+LDH in cell lysate)]×100 (Koh and Choi, 1987, *J Neurosci Methods* 20: 83-90).

The results showed that in HCT-8 cells with ARL-1 knockdown the cell death induced by acrolein was featured with LDH efflux and annexin V staining, a characteristic of oncosis.

Anchorage-independent growth in soft agar, an art-recognized characteristic of oncogenically-transformed cells, was also assessed in ARL-1 siRNA-containing HCT-8 cells. In these experiments, 100 cells/well in a 24-well plate were suspended in 0.5 mL of 0.3% Noble agar (Sigma, Mo.) and layered over 0.5 mL of 0.5% agar in the same medium. After being cultured at 37° C., 5% $CO_2$ for 2 weeks, cell foci were photographed and scored under inverted microscope. Clonogenic efficiency was calculated as: clonogenic efficiency (%)=(number of clones/number of seeded cells)×100 (Li et al., 2004, *Cancer Res.* 64: 7058-7064).

Figures 8A, 8B:
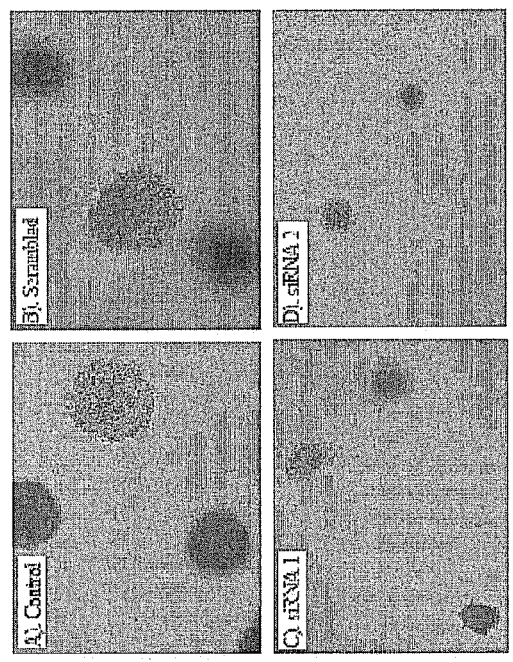
FIGS. 8A and 8B show photomicrographs of anchorage-independent growth of HCT-8 cells. HCT-8 cells were transfected with siRNA (50 nM) as described in Example 4 and grown in soft agar. Two weeks later, formed foci were photographed (FIG. 8A) and scored (FIG. 8B). Values in FIG. 8B represent mean±SD from three independent experiments.

The results of these experiments are shown in FIGS. 8A and 8B. The ARL-1 knockdown dramatically reduced the viability and clonogenic growth of HCT-8 cells. Focus formation rate and size of HCT-8 cells with ARL-1 knockdown were significantly reduced compared with controls. These result support the evidence set forth herein that ARL-1 protected cells from endogenous carbonyl lesions.

To verify phenotypic specificity to ARL-1, an EGFP/ARL-1 fusion protein was transiently expressed in 293T cells to assess cell response to acrolein exposure. 293T cells were purchased from American Type Culture Collection, grown and maintained in DMEM medium supplemented with 10% fetal bovine serum (FBS), 2 mM glutamine, and 100 U/ml penicillin and 100 µg/mL streptomycin at 37° C., 5% $CO_2$. In these experiments, a eukaryotic expression vector of EGFP/ARL-1 fusion protein was constructed by inserting ARL-1 cDNA (Cao et al., 1998, Id.) into the expression plasmid EGFP-C3 (Promega, WI) at Pst I and Apa I sites in the vector. Plasmid DNA was isolated and delivered into 293T cells using LipofectAMINE, following manufacturer's instruction (Invitrogen, CA).

Figures 9A, 9B, 9C:
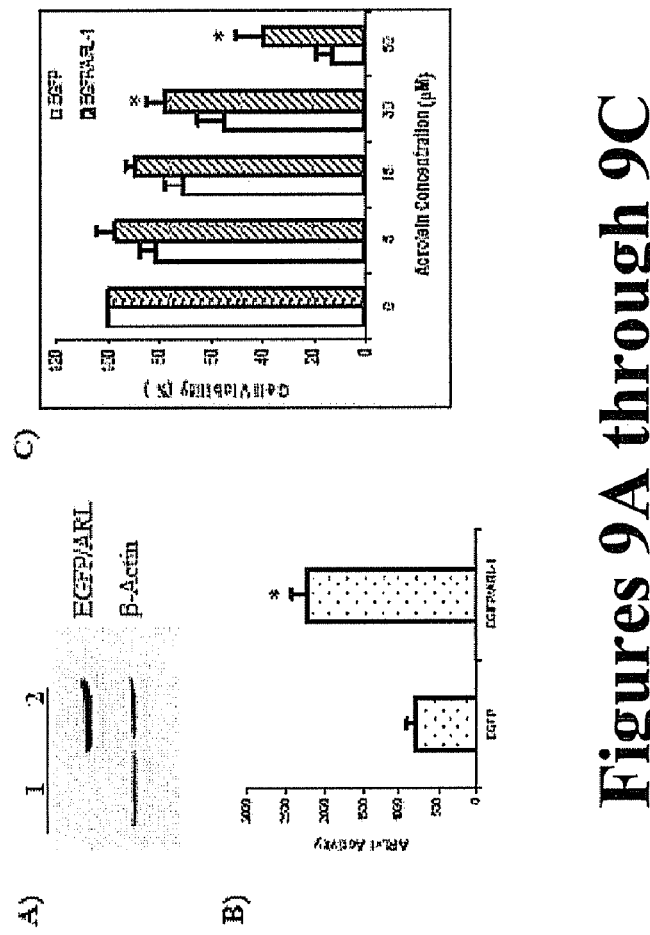
FIGS. 9A through 9C show protection by ARL-1 of 293T cells from acrolein toxicity. 293T cells were harvested for Western blot (FIG. 9A) and ARL-1 activity assays (nmol/mg protein/hour) (FIG. 9B) 36 hours after transfection with EGFP (control) or EGFP/ARL-1 plasmid DNA. For acrolein cytotoxicity tests, cells ($3 \times 10^3$) were spread into 96-well plates 24 hours after transfection. The next day, cells were fed with fresh medium containing acrolein at concentrations as indicated. Viable cells were evaluated by MTT kit (Roche, Ind.) following manufacturer's instructions. Results were expressed at percentage of control (FIG. 9C). Values in FIGS. 9B and 9C represent mean±SD from three independent experiments. * indicates statistical significance ($P<0.05$), compared to EGFP vector control. Lane 1, EGFP vector control, and lane 2, EGFP/ARL-1 fusion protein

The results of these experiments are shown in FIGS. 9A through 9C. EGFP/ARL-1 fusion protein was successfully expressed in 293T cells as shown by Western blot analysis in FIG. 9A. Cells containing these constructs had strong ARL-1 activity, indicating functionality of this fusion protein. Using these ARL-1 transferred cells, the cellular response to acrolein, administered at concentrations ranging from 5-50 µM, was assessed. A comparison between cells overexpressing ARL-1 and vector cells indicated that ARL-1 was capable of protecting cells from acrolein cytotoxicity at the concentrations tested (FIG. 9C).

Figure 10:
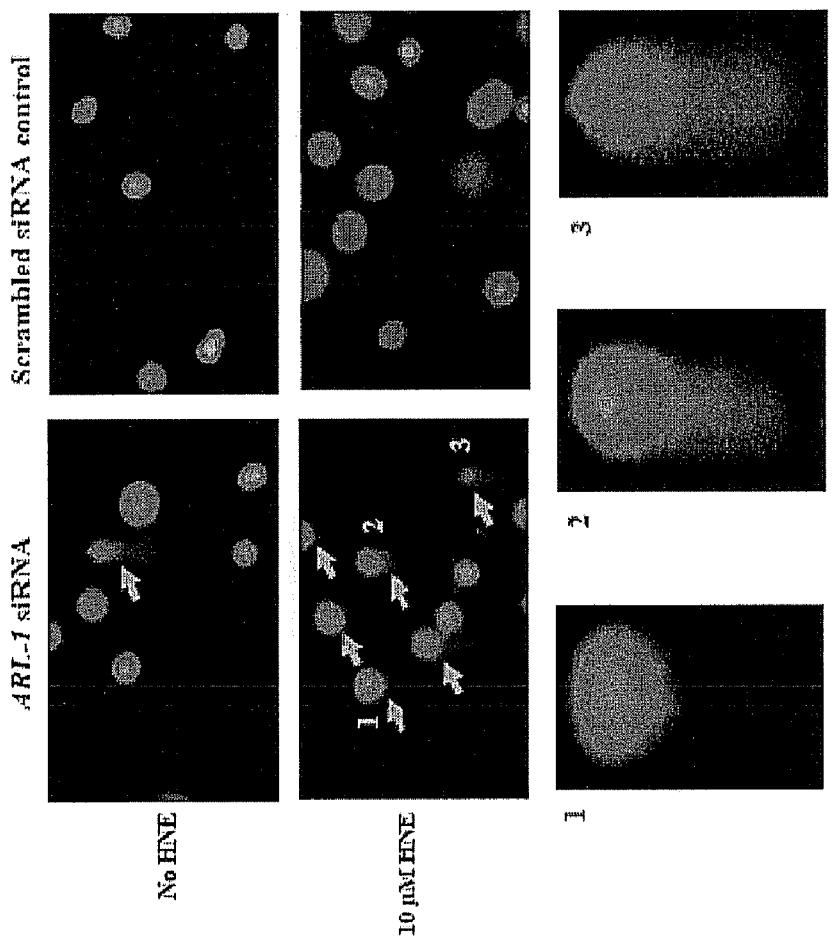
FIG. 10 shows the results of a comet assays for DNA breaks in HCT-8 cells with ARL-1 gene silencing. Results indicate that ARL-1 silencing led to DNA breaks (arrow, top panel). When the ARL-1 silenced cells were exposed to HNE, DNA breaks were dramatically increased (arrows, middle panel). Length and shape of comet tails reflect extent of DNA breaks (bottom panel).

Another assay for the capacity of reactive carbonyl species to have deleterious effects on colon epithelial cells detects the presence of DNA breaks in these cells, a well known factor of cell carcinogenesis. 4-hydroxynonenal (HNE) exposure was performed by incubating HCT-8 cells with 50 µM HNE in serum free medium for 1 hour, followed by incubation for 12 hours in regular medium containing 10% FBS. Comet assay was used for detection of the DNA breaks. These results indicated that silencing of ARL-1 resulted in DNA breaks and the DNA breaks were dramatically enhanced when exposed to HNE (FIG. 10). These data indicate the critical role of ARL-1 in protecting HCT-8 cells from DNA breaks that occurred automatically or are induced by HNE.

These results established that ARL-1 has the capacity to detoxify reactive carbonyl species in vitro and in vivo and that loss of function for this enzyme is associated with reduced growth and cell death. These results are also consistent with loss of function existing in a significant proportion of precancerous lesions and cancers in the gastrointestinal tract, and thus provide a target for diagnostic and chemopreventive interventions.

Example 5

Analysis of ARL-1 Function on Drug Resistance of Cancer

Figure 11A:
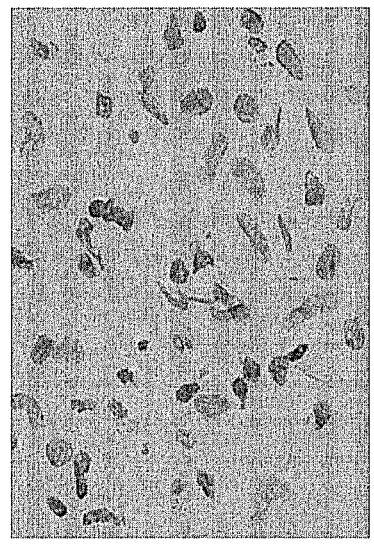
FIG. 11 shows the results of immunohistochemistry of human hepatocellular carcinoma using the anti-ARL-1 antibodies of the invention. Frozen sections of a human hepatocellular carcinoma tissue was stained with the specific ARL-1 antibody (A) (Arrow). An adjacent section was used for negative control (B), in which ARL-1 primary antibody was replaced by PBS. Hematoxylin counter staining was used to demonstrate nuclei.
Figure 11B:
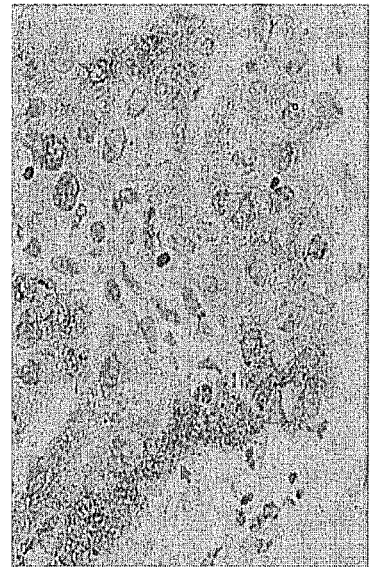

ARL-1 is a strong protein enzyme toward carbonyls, by reducing the carbonyl groups. Many anticancer agents contain active carbonyl group, such as anthracyclines (daunorubicin and doxorubicin). Therefore, ARL-1 may be implicated in the drug resistance of cancer cells that overexpress this protein, such as hepatocellular carcinoma (HCC; Cao et al., 1998, *J Biol Chem.* 273: 11429-11435) and lung cancer (Fukumoto et al., 2005, Id.). Immunohistochemistry was performed on frozen sections of HCC tissues, using the specific ARL-1 antibodies of the invention, and showed high expression of ARL-1 protein in hepatocellular carcinoma tissues (FIGS. 11A and 11B).

Biochemical experiments were performed to assess the biological activity of purified recombinant ARL-1 protein in detoxifying daunorubicin to its alcohol form, daunorubicinol. In this study, ARL-1 protein (2 µg/mL) was incubated with 10 mM daunorubicin at 30° C. for 20 min, in the presence of 0.2 mM NADPH, 0.4 M $Li_2SO_4$, and 135 mM sodium phosphate (pH 6.4). Enzymatic products were analyzed with a liquid chromatography-mass spectrometry. Briefly, the reaction mixture was filtered with a 5 kD filter to remove proteins and other macromolecules, and then diluted with acetonitrile (1:3). After being well mixed, this solution was further diluted with 5 mM ammonium acetate/acetonitrile. Daunorubicin and its enzymatic product (marked as X in FIGS. 12A and 12B) were separated and characterized using reversed-phase high-performance liquid chromatography (HPLC) with electron spray ionization tandem mass spectrometry (LC-MS).

Figure 12A:
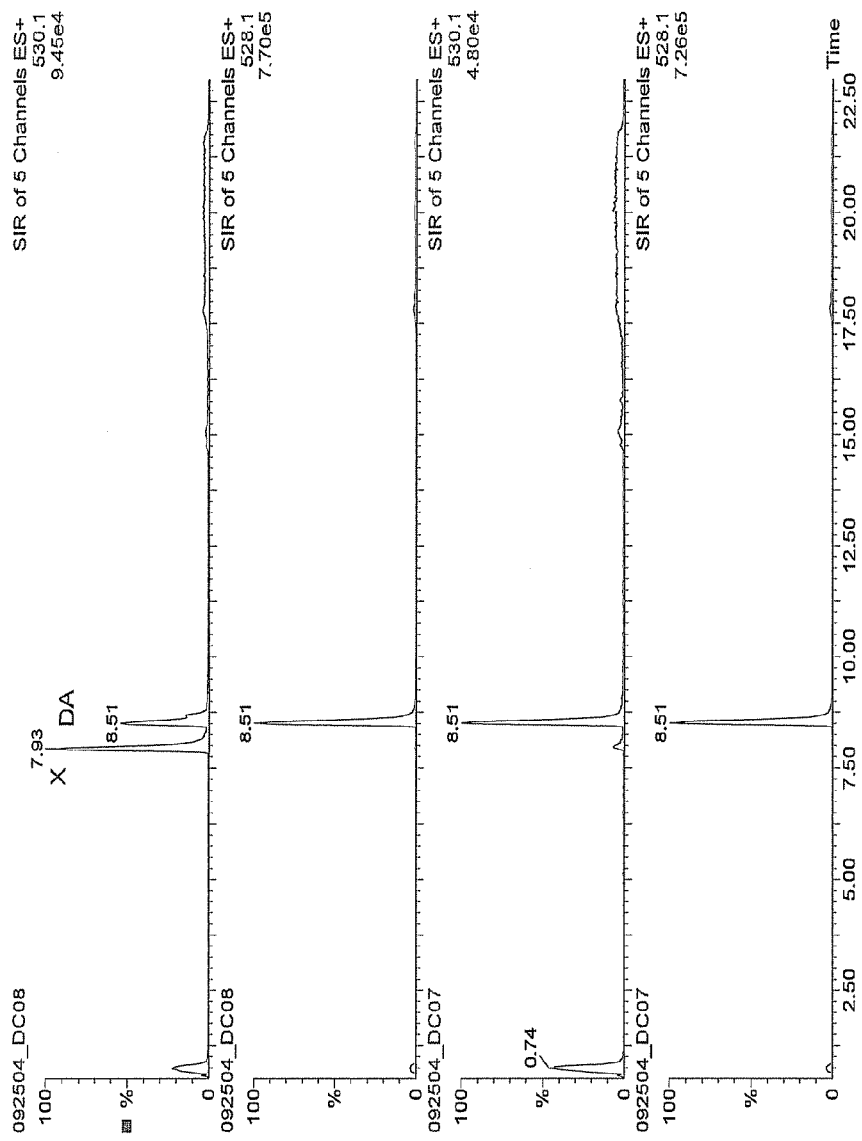
FIG. 12A shows the results of LC-MS analysis of daunorubicin analytes in a reaction mixture with purified, recombinant ARL-1 protein. Small molecule metabolites were assays using selective ion recording (SIR) mode monitoring ion transitions. A peak with m/z 530.1 in daunorubicin (DA) and ARL-1 reaction mixture (two upper traces) is 30 times higher than that in daunorubicin control (two lower traces).
Figure 12B:
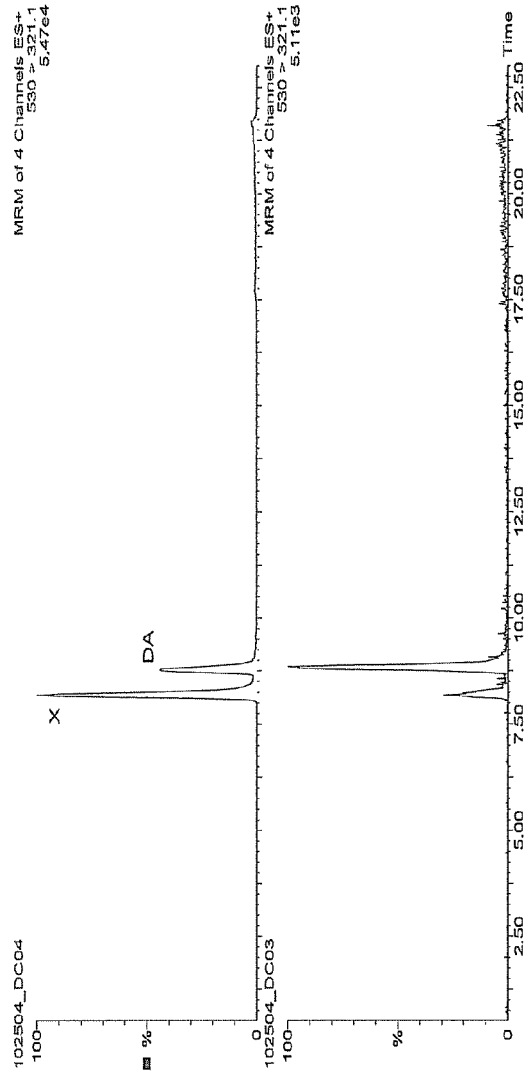
FIG. 12B shows the results of multiple reaction monitoring (MRM) mode monitoring ion transitions. This different monitoring method confirms the presence of reductive product with m/z 530.1 (top, reactants), compared with its parental mass 528.1 (lower, control).

The instrument used was a micromass triple quadrapole mass spectrometer (Waters, Milford, Mass.), operated in a positive ionization mode with a unit mass resolution. Resulting ions were first monitored using the selective ion recording (SIR) mode (FIG. 12A). Ion transitions, m/z 528.1 (MH$^+$) to 321.1 and 530.1 to 321.1 or 323.1, were monitored in multiple reaction monitoring (MRM, second order MS) mode (FIG. 12B). Capillary and cone voltages were set at 4.3 kV and 33 V, respectively. Source and desolvation temperatures were 120° C. and 325° C., respectively. Electron spray gas was provided with a high pressured liquid nitrogen tank. For MRM, argon of ultra high purity was used as the collision gas. A Waters HPLC system (Waters, Milford, Mass.) with a reversed phase, C18 column 2×50 mm was used, at a flow rate of 0.2 ml/min. Chromatographic separation was carried out with a gradient elution, from 5% to 95% acetonitrile for 20 min.

FIG. 12A shows the results from SIR analysis. Two upper traces from the reaction mixture of daunorubicin and ARL-1 show an ion ratio (530.1/528.1) for daunorubicin of approximately 6.63%, which is in agreement with the ratio of 6.61% shown in two lower traces from the control of daunorubicin alone (without ARL-1). It is important to note the peak with a retention time of 7.93 min (marked with X in FIGS. 12A and 12B). This peak is only present in the daunorubicin reactant sample, and is well separated from daunorubicin's peak, which has retention time of 8.51 min. This peak is only detectable with m/z 530.1 (indicating addition of two hydrogen protons), and its amount in the daunorubicin reactant sample is approximately 30 times more in height than in the daunorubicin control. This data indicates that this peak, with m/z 530.1, may represent the reduced products of daunorubicin (m/z 528.1).

This hypothesis was confirmed using an additional MRM analysis. FIG. 12B displays the presence of the reduced products with an ion transition of 530.1 to 321.1, showing the same amount of increase (approximately 30 times) in the daunorubicin and ARL-1 mixture (upper panel), compared to the daunorubicin control (lower panel). Furthermore, m/z 530.1 gives an ion transition of 321.1, rather than 323.1 (FIG. 12B), indicating that this reduction occurred on the $C_{13}$ ketone group ($COCH_3$) of daunorubicin, producing daunorubicinol. In view of the stronger cardiotoxicity of daunorubicinol rather than its antitumor activity, this finding may imply that the tumor-specifically induced ARL-1 may not only result in tumor drug resistance, but also contribute to cardiovascular side effects.

These results indicated that ARL-1 overexpressed in hepatocellular carcinoma can catalyze the reduction of daunorubicin, one of anthracyclines with C13 ketonic group, to its alcohol form, daunorubicinol. Daunorubicinol, and also, the alcohol forms of other anthracyclines have less antitumor activity but strong cardiovascular toxicity. Therefore, cancer with ARL-1 overexpression is unlikely to be suitable for treatment of anthracyclines, and it would be advantageous for patients to screen ARL-1 expression before beginning a fruitless course of chemotherapy.

It should be understood that the foregoing disclosure emphasizes certain specific embodiments of the invention and that all modifications or alternatives equivalent thereto are within the spirit and scope of the invention as set forth in the appended claims.

---

I claim:

1. An isolated antibody or antigen-binding fragment thereof that specifically binds to human ARL-1 protein, wherein the isolated antibody is produced by immunizing an animal using a peptide antigen consisting of the amino acid sequence identified by SEQ ID NO:1, and wherein the antibody is a monoclonal antibody.

2. An antibody of claim 1 that specifically binds to an epitope from the amino acid sequence identified by SEQ ID NO: 1.

3. A method for detecting human ARL-1 protein comprising the steps of contacting a sample comprising human ARL-1 protein with an antibody of claim 1 and detecting binding of the antibody with the protein.

4. The method of claim 3, wherein the sample is tissue or cells from stomach, small intestine, colon, liver, lung cancer or breast cancer.

5. A method of claim 3, wherein the human ARL-1 protein is detected in a tissue sample.

6. A method of claim 5, wherein the human ARL-1 protein is detected by in situ immunohistochemistry.

7. A method of claim 3, wherein the human ARL-1 protein is detected by Western blot analysis.

8. A method for detecting expression of human ARL-1 protein comprising the steps of contacting human ARL-1 protein with an antibody of claim 1 and detecting binding of the antibody with the protein.

9. A method of claim 8, wherein the human ARL-1 protein is detected in a tissue sample.

10. A method of claim 9, wherein the human ARL-1 protein is detected by in situ immunohistochemistry.

11. A method of claim 8, wherein the human ARL-1 protein is detected by Western blot analysis.

12. A method for identifying colon cancer or precancerous lesions of the colon, comprising the steps of contacting, with an antibody of claim 1, a normal colon epithelium sample and a colon biopsy sample from a human; detecting binding of the antibody with ARL-1 protein in the samples, thereby detecting ARL-1 protein expression, wherein colon cancer or a precancerous lesion of the colon is identified when ARL-1 protein expression is absent or lower in the colon biopsy sample than in the normal colon epithelium sample.

13. A method of claim 12, wherein the human ARL-1 protein is detected by in situ immunohistochemistry.

14. A method of claim 12, wherein the human ARL-1 protein is detected by Western blot analysis.

15. A method for detecting a precancerous lesion in a human gastrointestinal tract biopsy sample, comprising the steps of contacting, with an antibody of claim 1, a normal human gastrointestinal tract sample and a gastrointestinal tract biopsy sample from a human; detecting binding of the antibody with ARL-1 protein in the samples, thereby detecting ARL-1 protein expression, wherein a precancerous lesion of the gastrointestinal tract is identified when ARL-1 protein expression is absent or lower in the gastrointestinal biopsy sample than in the normal human gastrointestinal tract sample.

16. A method of claim 15, wherein the human ARL-1 protein is detected by in situ immunohistochemistry.

17. A method of claim 15, wherein the human ARL-1 protein is detected by Western blot analysis.

18. A method for identifying a human with colon cancer or precancerous lesions of the colon, comprising the steps of contacting, with an antibody of claim 1, a normal human colon epithelium sample and a colon biopsy sample from the human; detecting binding of the antibody with ARL-1 protein samples, thereby detecting ARL-1 protein expression, wherein a human with colon cancer or precancerous lesions of the colon is identified when ARL-1 protein expression is absent or lower in the colon biopsy sample from the human than in the normal human colon epithelium sample.

19. A method of claim 18, wherein the human ARL-1 protein is detected by in situ immunohistochemistry.

20. A method of claim 18, wherein the human ARL-1 protein is detected by Western blot analysis.

21. A method for identifying a human at risk for developing a gastrointestinal cancer, comprising the steps of contacting, with an antibody of claim 1, a histologically-normal human gastrointestinal sample and a precancerous lesion sample from the human; detecting binding of the antibody with ARL-1 protein in the samples, thereby detecting ARL-1 protein expression, wherein a human with a risk of gastrointestinal cancer is identified when ARL-1 protein expression is absent or lower in the precancerous lesion sample than in the histologically-normal human gastrointestinal sample.

22. A method of claim 21, wherein the human ARL-1 protein is detected by in situ immunohistochemistry.

23. A method of claim 21, wherein the human ARL-1 protein is detected by Western blot analysis.

24. A kit comprising a preparation of an antibody or antigen-binding fragment thereof according to claim 1 and instructions.

25. A kit according to claim 24, further comprising reagents for performing an immunological assay.

26. A method for identifying breast cancer or precancerous lesions of the breast, comprising the steps of contacting, with an antibody of claim 1, a normal breast epithelium sample and a breast biopsy sample from a human; detecting binding of the antibody with ARL-1 protein in the samples, thereby detecting ARL-1 protein expression, wherein breast cancer or a precancerous lesion of the breast is identified when ARL-1 protein expression is higher in the breast biopsy sample than in the normal breast epithelium sample.

27. A method of claim 26, wherein the human ARL-1 protein is detected by in situ immunohistochemistry.

28. A method of claim 26, wherein the human ARL-1 protein is detected by Western blot analysis.

29. A method for identifying a human at risk for developing a breast cancer, comprising the steps of contacting, with an antibody of claim 1, a histologically-normal human breast sample from the human, and a sample of normal human breast tissue; detecting binding of the antibody with ARL-1 protein in the samples, thereby detecting ARL-1 protein expression, wherein a human with a risk of breast cancer is identified when ARL-1 protein expression is higher in the histologically-normal human breast sample from the human than in the sample of normal human breast tissue.

30. A method of claim 29, wherein ARL-1 protein is detected by in situ immunohistochemistry.

31. A method of claim 29, wherein the human ARL-1 protein is detected by Western blot analysis.

32. An antibody of claim 1 wherein the antibody is a chimeric, humanized or CDR-grafted antibody or antigen-binding fragment thereof.

33. A kit according to claim 24, further comprising a control sample.

34. A kit according to claim 33, wherein the control sample is derived from a normal tissue of the gastrointestinal tract, liver, lung, or breast.

35. A kit according to claim 33, wherein the control sample is derived from blood, urine or stool.

36. An isolated antibody or antigen-binding fragment thereof that specifically binds to an epitope defined by the amino acid sequence as identified by SEQ ID NO:1, wherein the antibody is a monoclonal antibody.

37. An antibody of claim 36 wherein the antibody is a chimeric, humanized or CDR-grafted antibody or antigen-binding fragment thereof.

38. A kit comprising a preparation of an antibody or antigen-binding fragment thereof according to claim 36 and instructions.

39. A kit according to claim 38, further comprising reagents for performing an immunological assay.

40. A kit according to claim 38, further comprising a control sample.

41. A kit according to claim 40, wherein the control sample is derived from a normal tissue of the gastrointestinal tract, liver, lung, or breast.

42. A kit according to claim 40, wherein the control sample is derived from blood, urine or stool.

43. A method for detecting human ARL-1 protein comprising the steps of contacting a sample comprising human ARL-1 protein with an antibody of claim 36 and detecting binding of the antibody with the protein.

44. The method of claim 43, wherein the sample is tissue or cells of stomach, small intestine, colon, liver, lung cancer or breast cancer.

45. A method of claim 43, wherein the human ARL-1 protein is detected in a tissue sample.

46. A method of claim 45, wherein the human ARL-1 protein is detected by in situ immunohistochemistry.

47. A method of claim 43, wherein the human ARL-1 protein is detected by Western blot analysis.

48. A method for detecting expression of human ARL-1 protein comprising the steps of contacting human ARL-1 protein with an antibody of claim 36 and detecting binding of the antibody with the protein.

49. A method of claim 48, wherein the human ARL-1 protein is detected in a tissue sample.

50. A method of claim 49, wherein the human ARL-1 protein is detected by in situ immunohistochemistry.

51. A method of claim 48, wherein the human ARL-1 protein is detected by Western blot analysis.

52. A method for identifying colon cancer or precancerous lesions of the colon, comprising the steps of contacting, with an antibody of claim 36, a normal colon epithelium sample and a colon biopsy sample from a human; detecting binding of the antibody with ARL-1 protein in the samples, thereby detecting ARL-1 protein expression, wherein colon cancer or a precancerous lesion of the colon is identified when ARL-1 protein expression is absent or lower in the colon biopsy sample than in the normal colon epithelium sample.

53. A method of claim 52, wherein the human ARL-1 protein is detected by in situ immunohistochemistry.

54. A method of claim 52, wherein the human ARL-1 protein is detected by Western blot analysis.

55. A method for detecting a precancerous lesion in a human gastrointestinal tract biopsy sample, comprising the steps of contacting, with an antibody of claim 35, a normal human gastrointestinal tract sample and a gastrointestinal tract biopsy sample from a human; detecting binding of the antibody with ARL-1 protein in the samples, thereby detecting ARL-1 protein expression, wherein a precancerous lesion of the gastrointestinal tract is identified when ARL-1 protein expression is absent or lower in the gastrointestinal biopsy sample than in the normal human gastrointestinal tract sample.

56. A method of claim 55, wherein the human ARL-1 protein is detected by in situ immunohistochemistry.

57. A method of claim 55, wherein the human ARL-1 protein is detected by Western blot analysis.

58. A method for identifying a human with colon cancer or precancerous lesions of the colon, comprising the steps of contacting, with an antibody of claim 36, a normal human colon epithelium sample and a colon biopsy sample from the human; detecting binding of the antibody with ARL-1 protein in the samples, thereby detecting ARL-1 protein expression, wherein a human with colon cancer or precancerous lesions of the colon is identified when ARL-1 protein expression is absent or lower in the colon biopsy sample from the human than in the normal human colon epithelium sample.

59. A method of claim 58, wherein the human ARL-1 protein is detected by in situ immunohistochemistry.

60. A method of claim 58, wherein the human ARL-1 protein is detected by Western blot analysis.

61. A method for identifying a human at risk for developing a gastrointestinal cancer, comprising the steps of contacting, with an antibody of claim 36, a histologically-normal human gastrointestinal sample and a precancerous lesion sample from the human; detecting binding of the antibody with ARL-1 protein in the samples, thereby detecting ARL-1 protein expression, wherein a human with a risk of gastrointestinal cancer is identified when ARL-1 protein expression is absent or lower in the precancerous lesion sample than in the histologically-normal human gastrointestinal sample.

62. A method of claim 61, wherein the human ARL-1 protein is detected by in situ immunohistochemistry.

63. A method of claim 62, wherein the human ARL-1 protein is detected by Western blot analysis.

64. A method for identifying breast cancer or precancerous lesions of the breast, comprising the steps of contacting, with an antibody of claim 36, a normal breast epithelium sample and a breast biopsy sample from a human; detecting binding of the antibody with ARL-1 protein in the samples, thereby detecting ARL-1 protein expression, wherein breast cancer or a precancerous lesion of the breast is identified when ARL-1 protein expression is higher in the breast biopsy sample than in the normal breast epithelium sample.

65. A method of claim 64, wherein the human ARL-1 protein is detected by in situ immunohistochemistry.

66. A method of claim 64, wherein the human ARL-1 protein is detected by Western blot analysis.

67. A method for identifying a human at risk for developing a breast cancer, comprising the steps of contacting, with an antibody of claim 36, a histologically-normal human breast sample from the human, and a sample of normal human breast tissue; detecting binding of the antibody with ARL-1 protein in the samples, thereby detecting ARL-1 protein expression, wherein a human with a risk of breast cancer is identified when ARL-1 protein expression is higher in the histologically-normal human breast sample from the human than in the sample of normal human breast tissue.

68. A method of claim 67, wherein ARL-1 protein is detected by in situ immunohistochemistry.

69. A method of claim 67, wherein the human ARL-1 protein is detected by Western blot analysis.

70. An isolated peptide consisting of the amino acid sequence of SEQ ID NO:1.

71. A method of making the antibody of claim 1 comprising the steps of immunizing an animal using a peptide antigen consisting of the amino acid sequence of SEQ ID NO: 1 and recovering the antibody.

72. A method of making the antibody of claim 36 comprising the steps of immunizing an animal using a peptide antigen consisting of the amino acid sequence of SEQ ID NO:1 and recovering the antibody.

* * * * *